United States Patent
Simon

(10) Patent No.: US 7,207,965 B2
(45) Date of Patent: Apr. 24, 2007

(54) SHUNT FOR THE TREATMENT OF GLAUCOMA

(75) Inventor: Gabriel Simon, Madrid (ES)

(73) Assignee: SOLX, Inc., Boston, MA (US)

( * ) Notice: Subject to any disclaimer, the term of this patent is extended or adjusted under 35 U.S.C. 154(b) by 0 days.

(21) Appl. No.: 10/869,166

(22) Filed: Jun. 16, 2004

(65) Prior Publication Data

US 2004/0254521 A1    Dec. 16, 2004

Related U.S. Application Data

(60) Provisional application No. 60/478,895, filed on Jun. 16, 2003.

(51) Int. Cl.
*A61M 5/00* (2006.01)

(52) U.S. Cl. .......................................................... 604/8

(58) Field of Classification Search .............. 604/8–10, 604/264–266, 523, 294, 521, 533, 537; 606/107–108, 606/1, 2, 4, 6, 10–11, 13–17; 424/400, 427–8, 424/DIG. 7; 607/1, 92, 88, 89; 623/23.7–23.71, 623/23.74, 902, 905, 1.1, 1.11
See application file for complete search history.

(56) References Cited

U.S. PATENT DOCUMENTS

| | | | |
|---|---|---|---|
| 2,134,152 A | 10/1938 | Schwarzmayr | |
| 3,159,161 A | 12/1964 | Ness | |
| 3,767,759 A | 10/1973 | Wichterle et al. | |
| 3,860,008 A | 1/1975 | Miner et al. | |
| 3,915,172 A | 10/1975 | Wichterle et al. | |
| 4,377,169 A | 3/1983 | Banks | |
| 4,391,275 A | 7/1983 | Fankhauser et al. | |
| 4,428,746 A | 1/1984 | Mendez | |
| 4,457,757 A | 7/1984 | Molteno | |
| 4,521,210 A * | 6/1985 | Wong ............................ | 604/8 |
| 4,558,698 A | 12/1985 | O'Dell | |
| 4,560,375 A | 12/1985 | Schulte et al. | |
| 4,604,087 A | 8/1986 | Joseph | |
| 4,633,866 A | 1/1987 | Peyman et al. | |
| 4,722,724 A * | 2/1988 | Schocket ....................... | 604/8 |

(Continued)

FOREIGN PATENT DOCUMENTS

EP    1353340 A1    10/2003

(Continued)

OTHER PUBLICATIONS

Broadley, Mark et al., "Guidelines for Specifying Metal Medical Tubing", Medical Design News, Mar. 2003, pp. 1-4, Penton Media Inc., Cleveland, OH.

(Continued)

*Primary Examiner*—Patricia M. Bianco
(74) *Attorney, Agent, or Firm*—Maine & Asmus

(57) ABSTRACT

A system is provided for reducing intraocular hypertension, the system having an implantable shunt, with a planar member having at least one microchannel disposed within the planar member. There is an inflow port disposed proximate to a first end of the microchannel and an outflow port disposed proximate to a second end of the microchannel. The inflow port is configured such that when the implantable shunt is implanted, the inflow port is located approximately within the region of an angle of an anterior chamber.

34 Claims, 28 Drawing Sheets

U.S. PATENT DOCUMENTS

| | | |
|---|---|---|
| 4,741,730 A | 5/1988 | Dormandy, Jr. et al. |
| 4,795,437 A | 1/1989 | Schulte et al. |
| 4,846,172 A | 7/1989 | Berlin |
| 4,850,955 A | 7/1989 | Newkirk |
| 4,957,481 A | 9/1990 | Gatenby |
| 5,053,006 A | 10/1991 | Watson |
| 5,129,895 A | 7/1992 | Vassiliadis et al. |
| 5,169,395 A | 12/1992 | Narciso, Jr. |
| 5,171,213 A | 12/1992 | Price, Jr. |
| 5,222,952 A | 6/1993 | Loertscher |
| 5,259,380 A | 11/1993 | Mendes et al. |
| 5,292,362 A | 3/1994 | Bass et al. |
| 5,338,291 A | 8/1994 | Speckman et al. |
| 5,342,370 A | 8/1994 | Simon et al. |
| 5,346,464 A | 9/1994 | Camras |
| 5,346,497 A | 9/1994 | Simon et al. |
| 5,370,641 A | 12/1994 | O'Donnell, Jr. |
| 5,372,595 A | 12/1994 | Gaasterland et al. |
| 5,385,541 A | 1/1995 | Kirsch et al. |
| 5,397,300 A | 3/1995 | Baerveldt et al. |
| 5,411,473 A | 5/1995 | Ahmed |
| 5,423,800 A | 6/1995 | Ren et al. |
| 5,431,646 A | 7/1995 | Vassiliadis et al. |
| 5,433,701 A | 7/1995 | Rubinstein |
| 5,434,878 A | 7/1995 | Lawandy |
| 5,454,796 A | 10/1995 | Krupin |
| 5,480,396 A | 1/1996 | Simon et al. |
| 5,520,621 A | 5/1996 | Edenbaum et al. |
| 5,549,596 A | 8/1996 | Latina |
| 5,549,598 A | 8/1996 | O'Donnell, Jr. |
| 5,573,544 A | 11/1996 | Simon et al. |
| 5,573,773 A | 11/1996 | Kis et al. |
| 5,576,013 A | 11/1996 | Williams et al. |
| 5,599,340 A | 2/1997 | Simon et al. |
| 5,601,094 A | 2/1997 | Reiss |
| 5,626,558 A | 5/1997 | Suson |
| 5,651,782 A | 7/1997 | Simon et al. |
| 5,676,679 A | 10/1997 | Simon et al. |
| 5,704,907 A | 1/1998 | Nordquist et al. |
| 5,707,986 A | 1/1998 | Miller et al. |
| 5,709,653 A | 1/1998 | Leone |
| 5,785,674 A | 7/1998 | Mateen |
| 5,851,225 A | 12/1998 | Lawandry |
| 5,865,831 A | 2/1999 | Cozean et al. |
| 5,882,327 A | 3/1999 | Jacob |
| 5,944,748 A | 8/1999 | Mager et al. |
| 5,958,348 A | 9/1999 | Bi et al. |
| 6,007,578 A | 12/1999 | Schachar |
| 6,030,411 A | 2/2000 | Lawandy |
| 6,050,970 A | 4/2000 | Baerveldt |
| 6,059,772 A | 5/2000 | Hsia et al. |
| 6,077,299 A | 6/2000 | Adelberg et al. |
| 6,095,147 A | 8/2000 | Hill et al. |
| 6,096,028 A | 8/2000 | Bahmanyar et al. |
| 6,102,045 A | 8/2000 | Nordquist et al. |
| 6,110,212 A | 8/2000 | Gregory |
| 6,142,990 A | 11/2000 | Burk |
| 6,186,628 B1 | 2/2001 | Van de Velde |
| 6,207,392 B1 | 3/2001 | Weiss et al. |
| 6,251,103 B1 | 6/2001 | Berlin |
| 6,261,256 B1* | 7/2001 | Ahmed .................. 604/9 |
| 6,344,272 B1 | 2/2002 | Oldenburg et al. |
| 6,355,046 B2 | 3/2002 | Kikuchi et al. |
| 6,423,056 B1 | 7/2002 | Ishikawa et al. |
| 6,428,811 B1 | 8/2002 | West et al. |
| 6,450,984 B1 | 9/2002 | Lynch et al. |
| 6,471,666 B1 | 10/2002 | Odrich |
| 6,520,955 B2 | 2/2003 | Reynard |
| 6,524,330 B1 | 2/2003 | Khoobehi et al. |
| 6,530,944 B2 | 3/2003 | West et al. |
| 6,544,208 B2 | 4/2003 | Ethier et al. |
| 6,589,203 B1 | 7/2003 | Mitrev |
| 6,600,951 B1 | 7/2003 | Anderson |
| 6,607,522 B1 | 8/2003 | Hamblin et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,736,791 B1 | 5/2004 | Tu et al. |
| 6,749,623 B1 | 6/2004 | Hsi et al. |
| 6,827,700 B2 | 12/2004 | Lynch et al. |
| 6,966,888 B2 | 11/2005 | Cullen et al. |
| 2002/0133168 A1 | 9/2002 | Smedley et al. |
| 2002/0156413 A1 | 10/2002 | Williams et al. |
| 2003/0212383 A1 | 11/2003 | Cote et al. |
| 2004/0015140 A1* | 1/2004 | Shields .................. 604/289 |
| 2004/0039378 A1 | 2/2004 | Lin |
| 2004/0193262 A1 | 9/2004 | Shadduck |
| 2004/0215126 A1* | 10/2004 | Ahmed .................. 604/9 |
| 2004/0225250 A1 | 11/2004 | Yablonski |
| 2004/0254517 A1 | 12/2004 | Quiroz-Mercado et al. |
| 2004/0260227 A1* | 12/2004 | Lisk et al. .................. 604/8 |
| 2005/0182350 A1 | 8/2005 | Nigam |
| 2005/0197613 A1 | 9/2005 | Sniegowski et al. |
| 2005/0273033 A1 | 12/2005 | Grahn et al. |
| 2005/0277865 A1 | 12/2005 | Gharib et al. |

FOREIGN PATENT DOCUMENTS

| | | |
|---|---|---|
| JP | 200411332 | 4/2004 |
| WO | 8400101 A1 | 1/1984 |
| WO | 9409837 A1 | 5/1994 |
| WO | 9417755 A1 | 8/1994 |
| WO | 9721406 A1 | 6/1997 |
| WO | 0030592 | 6/2000 |
| WO | 0071019 A1 | 11/2000 |
| WO | 0103599 A2 | 1/2001 |
| WO | 2004/008945 A2 | 1/2004 |
| WO | 2004/091696 A1 | 10/2004 |

OTHER PUBLICATIONS

"Aqueous Shunts—510(k) Submission", Nov. 16, 1998, pp. 1-20, U.S. Department of Health and Human Services.

* cited by examiner

SHUNT FOR THE TREATMENT OF GLAUCOMA

RELATED APPLICATIONS

This application claims the benefit of U.S. Provisional Application No. 60/478,895, filed Jun. 16, 2003. This application is herein incorporated in its entirety by reference.

FIELD OF THE INVENTION

The present invention pertains to surgical treatments for glaucoma and methods for reducing intraocular pressure (IOP), and more particularly relates to an implantable shunt device for allowing aqueous outflows from the eye's anterior chamber and associated methods thereof.

BACKGROUND OF THE INVENTION

Glaucoma is a major public health problem, affecting about two percent of the U.S. population and the third most common cause of blindness in the U.S. There are several forms of glaucoma however each results in elevated intraocular pressure (IOP) in the eye, which can cause progressive damage to the optic nerve, and both central and peripheral visual field loss. If the IOP remains high for an extended period of time, total vision loss can occur. The elevated IOP is caused by an imbalance in fluid inflows and outflows in the eye, and the pressure reduces the blood supply to the optic nerve. The principal objective of medical treatment is the lowering of intraocular pressure.

The anterior chamber of the eye contains the aqueous humor, a clear fluid that is produced continuously by the ciliary body around the lens. The constant flow of aqueous humor though the eye's front chamber exits through two different routes. A limited outflow occurs through the uveoscleral route, wherein fluid migrates outwardly between muscle fibers of the ciliary body. The primary aqueous outflow pathway is through the trabecular meshwork (TM) and the Schlemm's canal.

The trabecular meshwork is a filtering structure that extends around the circumference of the eye at the "angle"—the junction between the iris, sclera and cornea. The trabecular meshwork consists of layers of collagen webs that filter the outflows. The meshwork has a monolayer of trabecular cells that produce enzymes for degrading extracellular material that may be captured by the filtering structure.

Aqueous humor that passes through the trabecular meshwork flows into Schlemm's canal, which is a passageway or series of septae that extend around the circumference of the eye adjacent to the meshwork. The aqueous fluid thereafter flows through a series of collecting channels that drain from Schlemm's canal and into the episcleral venous system. In a normal eye, aqueous production by the ciliary body is equal to aqueous outflows to provide an IOP that remains constant in the 15 to 21 mm Hg range. In a patient suffering from glaucoma, the resistance through the outflow system is typically greater than 21 mm Hg. In primary open angle glaucoma (POAG), the most common form of glaucoma, the principal resistance to fluid outflow is centered about the region of trabecular meshwork that is adjacent Schlemm's canal. It is believed that an abnormal trabecular cell metabolism results in compacted meshwork layers or a build up of extracellular materials within the meshwork that inhibits fluid flows.

Numerous therapies have been developed for treating glaucoma by decreasing intraocular pressure. Pharmacological therapies include topical ophthalmic drops and oral medications that reduce the production of aqueous by the ciliary body or increase aqueous outflows via the uveoscleral route. The treatments generally require applications at least daily and are relatively expensive. Furthermore, drugs may have occasional serious side effects, such as blurred vision, allergic reactions, headaches and potentially dangerous interactions with other drugs.

Surgical approaches for treating open-angle glaucoma consist of laser trabeculoplasty, trabeculectomy, and the implantation of aqueous shunts. Trabeculectomy is a widely practiced surgery wherein microsurgical techniques are used to dissect the trabecular meshwork to allow more rapid aqueous outflow through the meshwork. The benefits of the dissection procedures diminish over time due to the body's wound healing response and resulting fibrosis that repairs and closes the dissected opening in the meshwork. After the dissections are healed up, the intraocular pressure again increases. Thus these expensive procedures do not provide a long-lasting cure.

Implantable shunts and surgical methods are also known for providing a fluid path for aqueous humor to exit the anterior chamber of the eye to the sclera or a space beneath the conjunctiva. See e.g., U.S. Pat. No. 6,050,970 to Baerveldt.

Trabeculectomies and shunt surgeries and variations thereof have several disadvantages and moderate success rates. Such surgeries require significant surgical skills to create an incision through the full thickness of the sclera into the subconjunctival space. Further, the surgeries cause substantial trauma to the eye. The procedures are generally performed in an operating room and have a prolonged recovery time. Thus, the state of the art shunts and surgical techniques have yet to provide a cost-effective and long-lasting solution which has short recovery periods and low risk.

What are needed, therefore, are devices and techniques for successful, long-term reduction in intraocular pressure.

SUMMARY OF THE INVENTION

One embodiment of the present invention provides a system for reducing intraocular hypertension, the system comprising an implantable shunt. The implantable shunt comprises a planar member and at least one microchannel disposed within the planar member. There is an inflow port disposed proximate to a first end of the microchannel and an outflow port disposed proximate to a second end of the microchannel, wherein the inflow port is configured such that when the implantable shunt is implanted, the inflow port is located about approximately within the region of an angle of an anterior chamber.

Another embodiment of the present invention provides such a system wherein the outflow port is disposed in a plane, that plane being chosen from the group consisting of a suprachoroidal plane and a suprascleral plane.

A further embodiment of the present invention provides such a system wherein the planar member has a thickness less than 50 microns.

Still another embodiment of the present invention provides such a system wherein the thickness of the planar member is between 5 and 25 microns.

A still further embodiment of the present invention provides such a system further comprising at least one anchor.

Even another embodiment of the present invention provides such a system wherein the anchor is selected from the group consisting of barbs, hooks, and sutures.

An even further embodiment of the present invention provides such a system further comprising at least one reservoir communicating with the first end of the microchannel. Yet another embodiment of the present invention provides such a system further comprising at least one reservoir communicating with the second end of the microchannel.

A yet further embodiment of the present invention provides such a system wherein the at least one microchannel comprises fewer than 200 microchannels. An even further embodiment provides such a system wherein the at least one microchannel comprises between 10 and 100 microchannels.

Still even another embodiment of the present invention provides such a system further comprising at least one sacrificial microchannel closure. A still even further embodiment of the present invention provides such a system wherein the closure is photo-ablatable. Yet even another embodiment of the present invention provides such a system wherein the closure is doped with chromophores.

Still yet another embodiment of the present invention provides such a system wherein the system is comprised of at least one biocompatible material selected from the group of biocompatible material consisting of gold, platinum, titanium, nickel, molybdenum, biocompatible metals, biocompatible metal alloys, biocompatible ceramics, biocompatible polymers and combinations thereof.

One embodiment of the present invention provides a method for the reduction of intraocular pressure in an eye of a subject, the method comprising providing an implantable planar microchannel shunt, implanting the shunt in the eye, such that a first end of the shunt is disposed proximate to an angle of an anterior chamber of the eye, and permitting aqueous flows to migrate from the anterior chamber through at least one microchannel disposed within the shunt.

Another embodiment of the present invention provides such a method further comprising photo-ablating tissue disposed between the first end and the anterior channel. A further embodiment provides such a method wherein photo-ablating tissue disposed between the first end and the anterior channel comprises retracting tissue anterior to the first end of the shunt, and photo-ablating an intervening tissue layer with a laser, such as an excimer laser or a titanium sapphire laser.

Even another embodiment of the present invention provides such a method further comprising photo-ablating a sacrificial microchannel closure, thereby increasing flow of the aqueous flow through the shunt. An even further embodiment provides such a method wherein photo-ablating the sacrificial microchannel closure comprises using a goniolens.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION OF THE INVENTION

One embodiment of the present invention comprises a thin planar shunt device that can have various shapes and configurations as depicted in FIGS. 1 through 6. Various embodiments of the shunts are adapted to cooperate with the introducer or delivery apparatus used to facilitate placement of the shunt into the patient's eye.

Figure 1A:
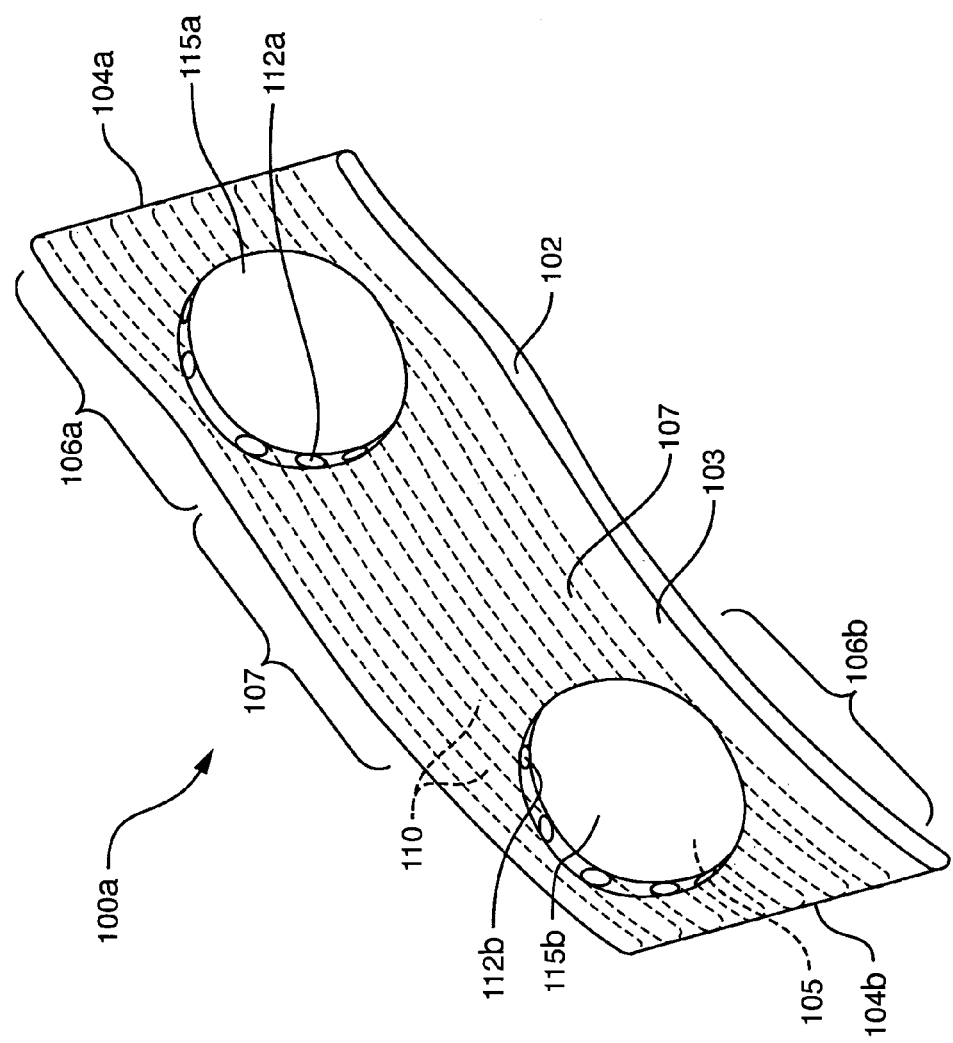
FIG. 1A is a perspective view of a shunt configured in accordance with one embodiment of the present invention.

Referring to FIG. 1, one embodiment of a shunt device 100A comprises a thin planar body 102 that extends along a longitudinal axis 105 from a first end section 106A to a second end section 106B with medial section 107 therebetween. The shape and configuration of the planar member, herein defined as its "planform", is shown as being substantially rectangular with relatively straight side edges 103 and endwise edges 104A, 104B. However, other shapes and configuration are well within the scope of the invention as is readily appreciated by one skilled in the art. For example, the first end section 106A can be bulbous or pointed as illustrative examples. Likewise, the second end section 106B and the medial section 107 can vary in shape and pattern. The side edges 103 as well as the endwise edges 104A, 104B can be fabricated to encompass sloping edges, ridges or other patterns in addition to straight edges. As described herein, the first end section 106A is generally defined as the end that is proximate the anterior chamber AC of the eye (the inflow end) and the second end 106B is more remote from the anterior chamber to direct aqueous flows outwardly.

In this particular embodiment the shunt device is shown having a substantially planar body 102. However, the various embodiments of the present invention encompass generally planar bodies including convex bodies, concave bodies, and bodies of variable thickness as well as substantially planar bodies. For example, the body 102 can employ a wedge shape such that the thickness of the first end section 106A differs from the thickness of the second end section 106B. This includes variations of thickness throughout the first end section 106A, the medial section 107 and the second end section 106B along the longitudinal axis 105 as well as from side to side.

Figure 1B:
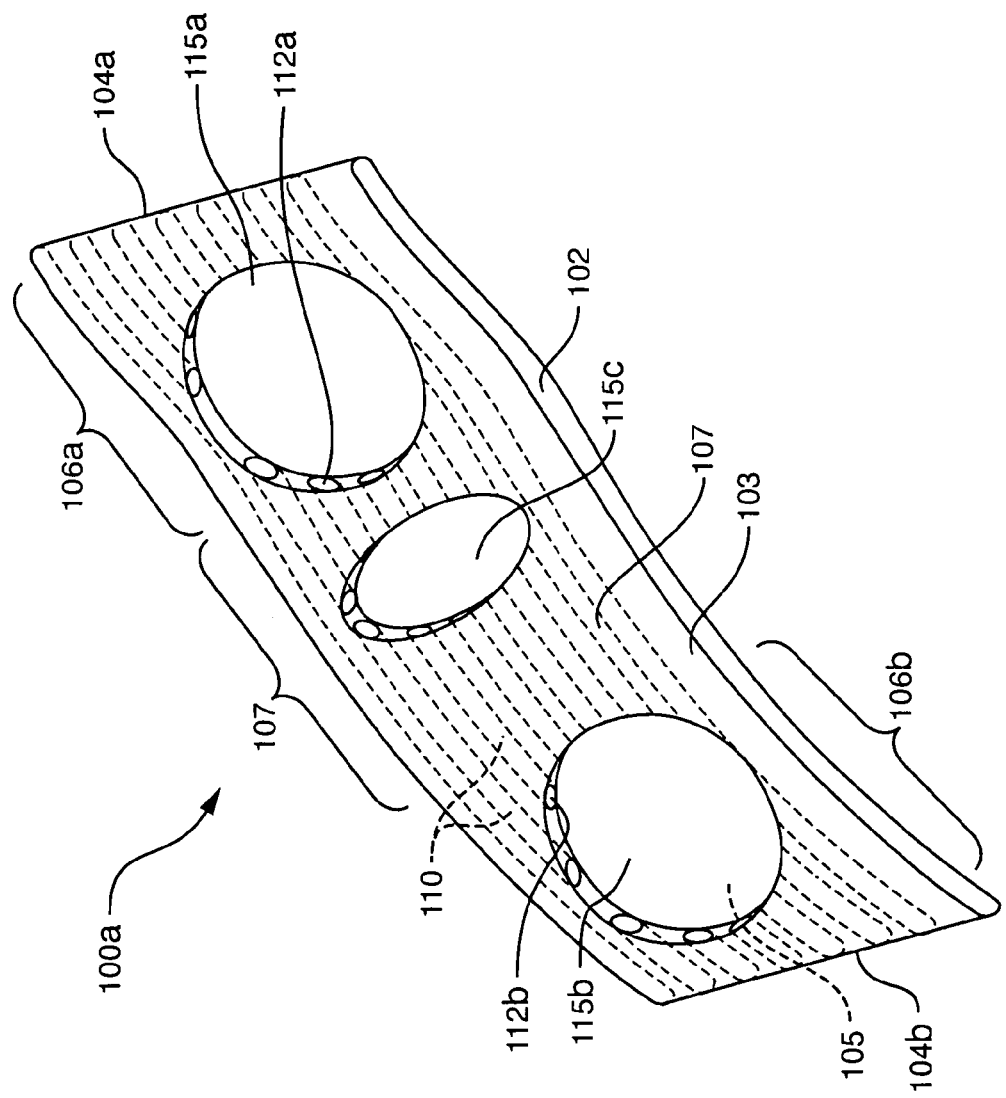
FIG. 1B is a perspective view of a shunt having a secondary reservoir configured in accordance with one embodiment of the present invention.
Figure 1C:
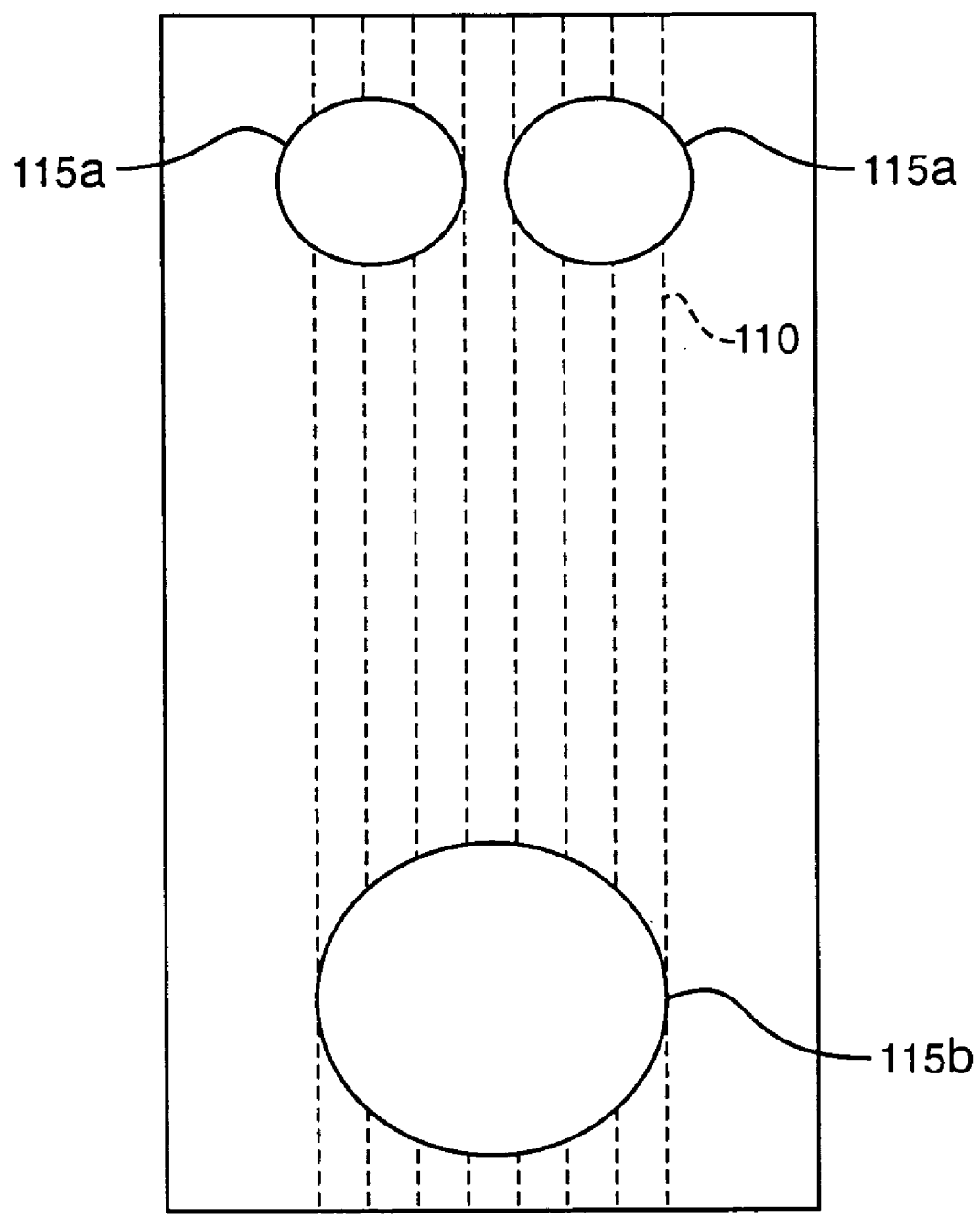
FIG. 1C is a plane view of a shunt having dual reservoirs configured in accordance with one embodiment of the present invention.

The shunt 100A has a plurality of microchannels 110 (collectively) each extending from an inflow port 112A in the first end section 106A to an outflow port 112B in the second end section 106B. The shunt 100A of FIG. 1 has open portions 115A and 115B therein, at times defined as "reservoirs" herein. As illustrated in FIGS. 1B and 1C, additional reservoirs may be provided. In this illustration there is a single inflow reservoir 115A and outflow reservoir 115B, however a plurality of reservoirs 115A, 115B in various shapes, sizes and patterns is within the scope of the invention. It should also be appreciated that the reservoirs shape and size are variable and couple the inflow port 112A to the outflow port 112B. The use of a combination of primary 115A and secondary reservoirs 115C, as in FIG. 1B, add flexibility to the design and use of the shunt.

In some embodiments there are one or more microchannels 110 that are coupled between the endwise edges 104A, 104B with or without intersecting the reservoirs 115A, 115B. The endwise edges 104A, 104B of the microchannels can be open to allow additional fluid flow or closed at the endwise edge 104A, 104B depending upon the application. It should also be understood that the microchannel thickness can be uniform or non-uniform to include aspects wherein the area of the microchannel at the inflow port 112A is different that the area of the microchannel at the outflow port 112B.

The inflow and outflow ports, 112A and 112B, of the microchannels 110 are disposed generally about the periphery of the open portions or reservoirs 115A and 115B. The open portions 115A and 115B, in some embodiments, are adapted to provide a sufficient spacing or area to help insure that tissue is not excessively compressed against the inflow and outflow ports 112A, 112B which might limit fluid flow through the microchannels 110. The placement, size and shape of the reservoirs 115A, 115B can be varied to establish a long-lasting and satisfactory flow of fluid.

As depicted in FIG. 1, the thin planar body 102 is deformable to conform to scleral curvature or other curves of dissected planes or spaces created for the implant body. In some embodiments, the shunt is fabricated of gold, which has been found to be suitably biocompatible. One skilled in the art will, however, appreciate that any other biocompatible composition, such as titanium, platinum, stainless steel, nickel, Nitinol, molybdenum and other biocompatible metals, metal alloys, ceramics, or polymers, or combinations thereof, are within the scope of the present invention. There are various combinations and permutations of alloy materials used for intravascular stents and one skilled in the art readily appreciates that such alloys are within the scope of the invention.

One embodiment of the present invention has been designed with the further aspect related to the prevention of wounds and intended to aid in the healing process. As in intravascular stents, coatings and additives may be applied, such as those used to prevent restenosis resulting from scarring and wound healing. Such coatings are familiar to one skilled in the art of medical devices, and may be mineral or ceramic coatings, pharmaceutical coatings, radiological coatings, polymer coatings, metallic coatings and combinations thereof. According to one embodiment, the use of selected materials and of any coatings is intended to reduce or minimize the attachment of tissue to the shunt and allow for fluidic flow about the shunt.

The shape of the shunt, according to one embodiment, has also incorporated certain features, such as rounded edges as opposed to sharp edges, to aid in preventing tissue from attaching to the shunt. Sharp edges on implants allow fibroblasts to adhere to the shunt, facilitating the growth of scar tissue around the shunt and the healing of the wound, while smooth edges do not provide such favorable sites for adhesion. Scar tissue is detrimental as is restricts flow of aqueous fluid into, out of, through and around the shunt, both from its increased density over ordinary structures in the angle of the anterior chamber, and from its healing of the wound. Fibroblasts may clog inlet ports and outlet ports of the shunt. The open wound itself permits the unobstructed flow of aqueous fluid into the shunt. The surgeon's adjustment of flow rate is, in part, effected by the unobstructed flow. Complete closure of the wound would inhibit the flow of aqueous, resulting in higher intraocular pressure than originally anticipated. Furthermore scarring around the shunt would complicate removal of the shunt should infection, clogging, or other occurrences render it inoperable and require its removal.

Figure 15:
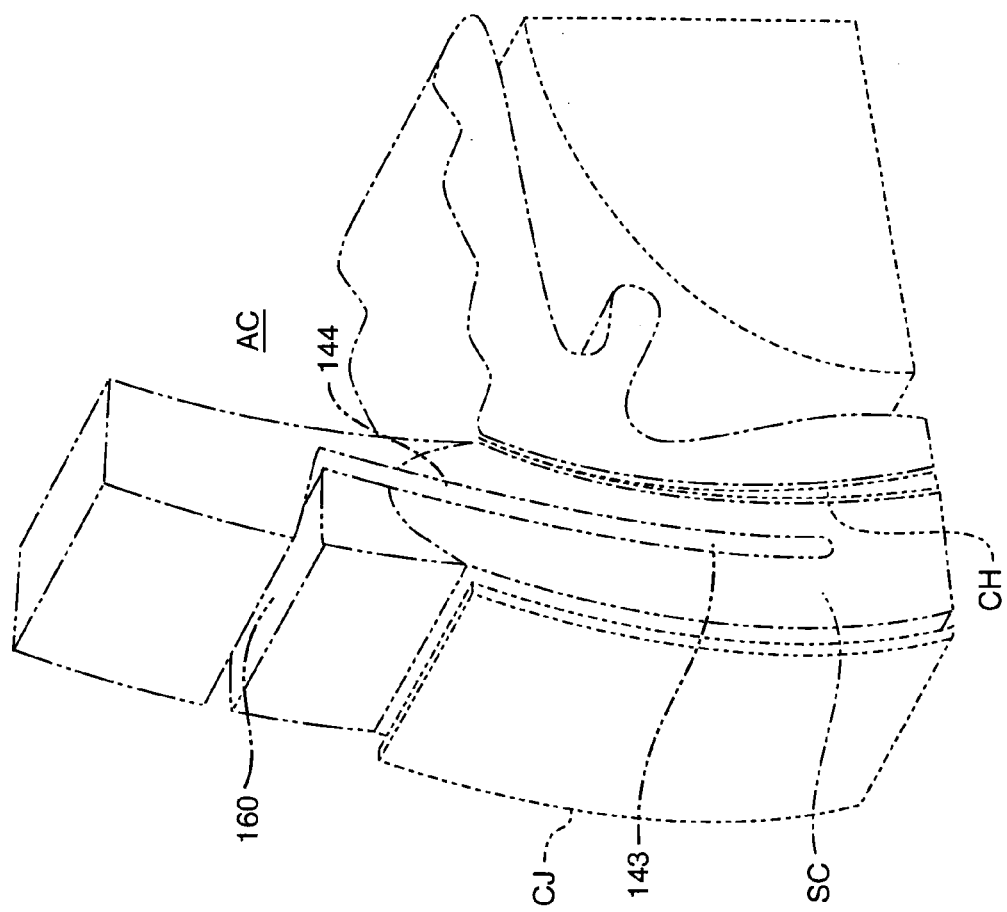
FIG. 15 illustrates the dissected plane following withdrawal of the blade.

In some embodiments, such as that illustrated in FIG. 15, a hydrophilic polymer or other polymer of high porosity 143 such as polyethylene oxide may be introduced to the incision 144 prior to, or in conjunction with implantation of the shunt. The polymer may, according to some embodiments, be introduced as a gel, such as those well known to those skilled in the art. The polymer 143 acts to augment flow of aqueous fluid in the region of the shunt.

Figure 2:
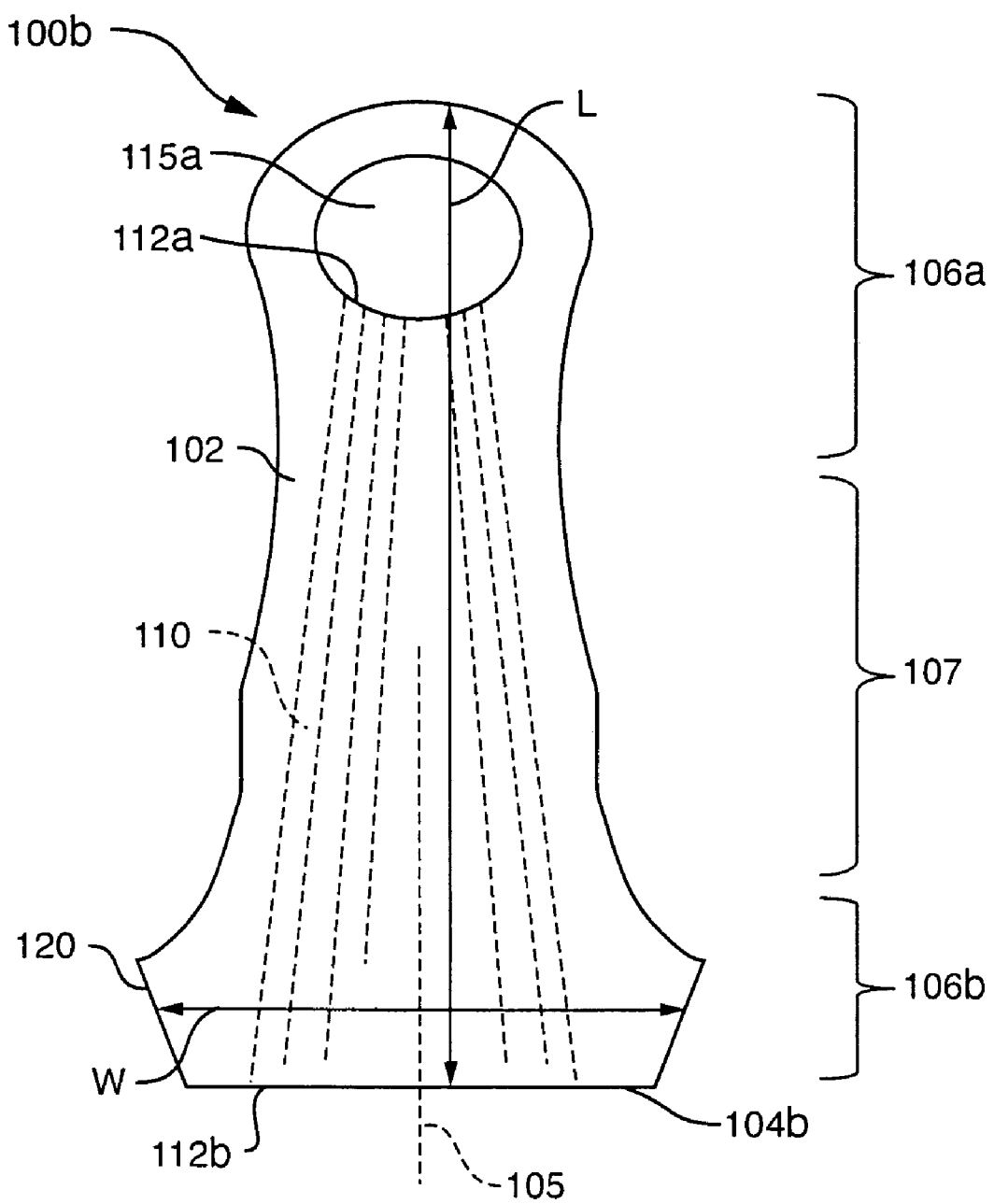
FIG. 2 is a plan view of a shunt configured in accordance with one embodiment of the present invention illustrating its planform with barb portions.

Now referring to FIG. 2, an alternative embodiment of shunt device 100B is shown in plan view that again comprises a planar body 102 that extends along longitudinal axis 105. In this embodiment, the first end section 106A again carries an opening or reservoir 115A within inflow ports 112A about its edge or periphery. The outflow ports 112B of the microchannels 110 in the second end section 106B are simply disposed in the edgewise edges 104B of the body 102. Thus, the scope of the invention extends to implants without the outflow reservoir 115B as in FIG. 1. In FIG. 2, it can be seen that the planform of the body includes at least one barb, hook, suture or other such anchor structure 120 for engaging tissue and for preventing migration of the implant body 102. The anchor structure 120 includes employing the shape of the body 102 such as varying the thicknesses of the first end section 106A, medial section 107 and second end section 106B for retaining the body and preventing migration.

The width W of the implant body 102 ranges, in various embodiments, between about 0.5 mm. and 5.0 mm, and according to one embodiment is from about 1.0 mm to 4.0 mm. The length L, in various embodiments, ranges between about 2.0 mm. and 10.0 mm, and, in some embodiments, is about approximately between 4.0 mm and 8.0 mm. The thickness of the shunt body ranges, in various embodiments and shapes, from about 2 microns to 50 microns, and, in some embodiments, is about approximately between 5 microns and 20 microns. The number of microchannels 110 in the shunt body typically can range from one to a hundred or more.

In one embodiment the shunt is intended for a target IOP in the range of 8–16 mmHg. This is a working range for the operation of the shunt and the shunt is designed accordingly. There are fluid dynamic principles that assist in determining the characteristics of the microchannels and the number of microchannels required for a given application utilizing variable such as the IOP pressure, flow rate and the properties of the liquid.

According to one embodiment, the shunt is designed to operate in the target IOP employing about 60% of the microchannels being open to the fluid flow and about 40% closed. This allows the doctor to open additional channels as described herein as necessary to optimally maintain the IOP in the target range, this permits modulation, or in situ adjustment of flow rates to achieve optimal intraocular pressure. As such, the implant is able to modulate the fluid flow once the shunt is inserted in the eye, not merely avoiding excessively low intraocular pressures.

Figure 3:
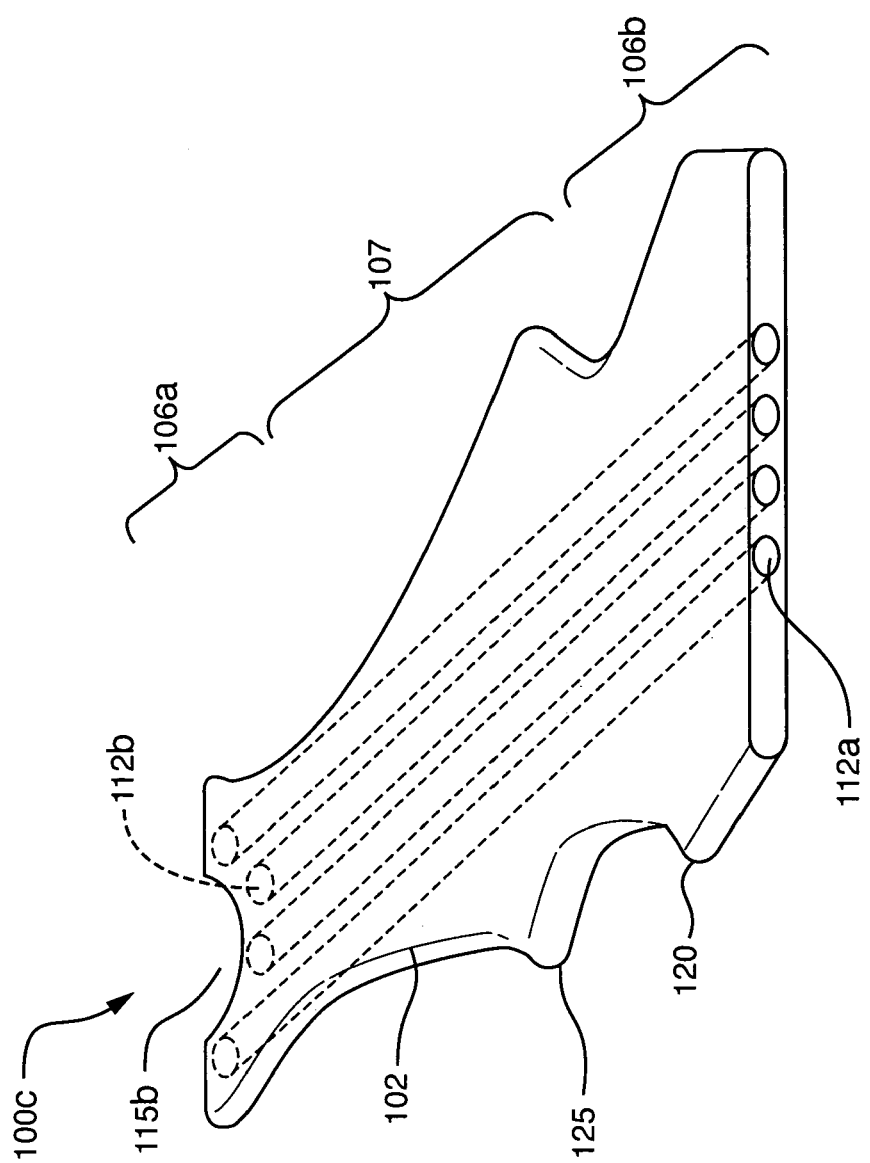
FIG. 3 is a perspective view of a shunt configured in accordance with one embodiment of the present invention illustrating its planform with barb portions facing both directions.

FIG. 3 shows an alternative embodiment of shunt 100C with a substantially planar body 102 having a planform that includes first and second barb elements 120 and 125 along each side of the shunt for engaging tissue and to prevent migration. In this embodiment, the second end section 106B carries an open portion 115B that is configured as a "scalloped" end which still functions as the reservoir in the embodiments of FIGS. 1 and 2, wherein the liquid flows from the inflow port 112A through the microchannels 110 and to the outflow port 112B. In this embodiment, the second end section 106B is linear or curved forming a partial or open reservoir 115B and the shunt 100C is adapted for placement in the angle of the anterior chamber as described herein.

Figure 4:
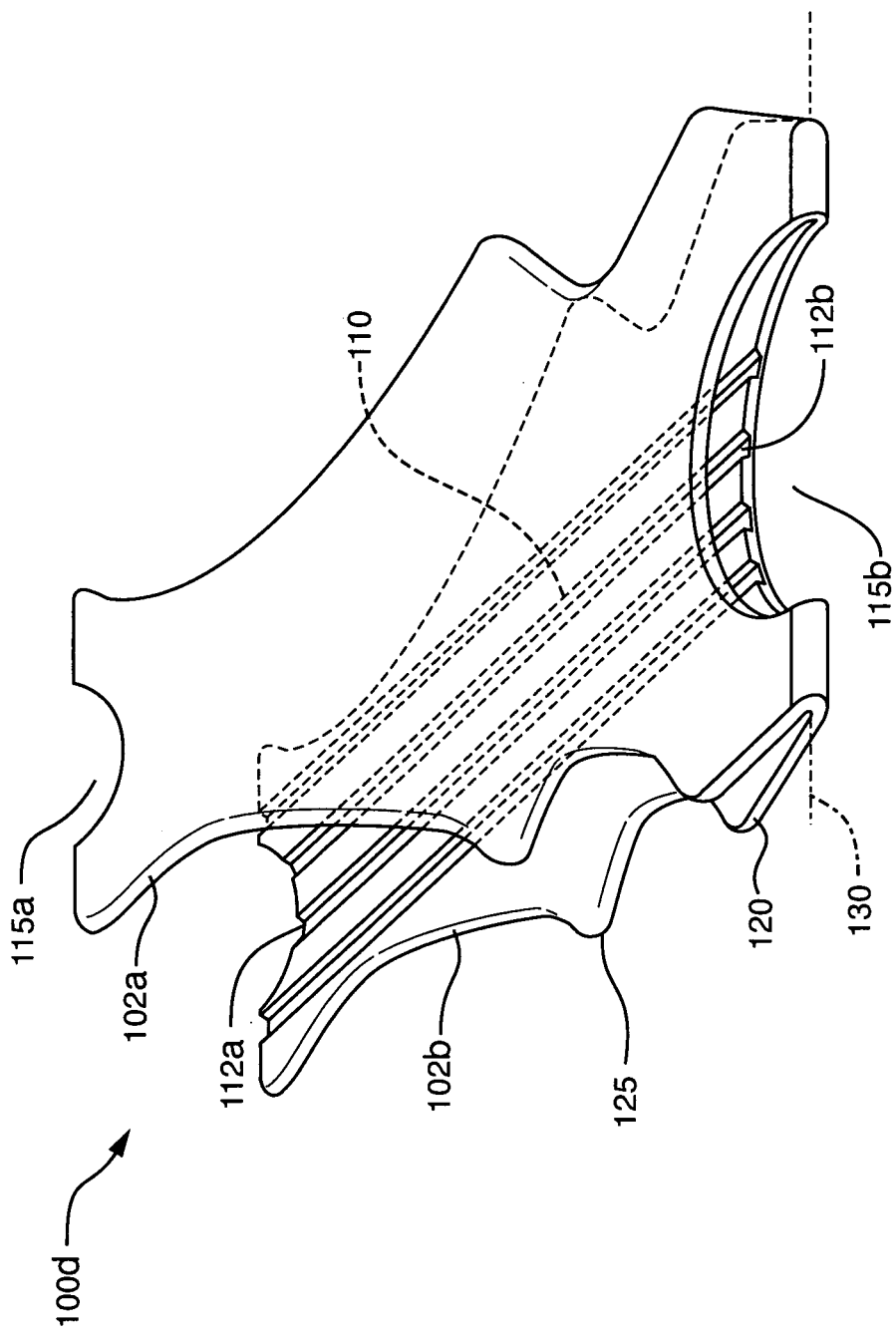
FIG. 4 is a perspective view of a shunt configured in accordance with one embodiment of the present invention illustrating a method of fabrication.

FIG. 4 shows an alternative shunt 100D and a method of fabrication wherein two planar body portions 102a and 102b that may be folded along line 130 to provide the finished shunt 100D forming a living hinge at the fold line 130. The microchannels 110 can be fabricated into one of the planar bodies, such as 102b, and allow the fluid flow from the inflow reservoir 115A to the outflow reservoir 115B. Some embodiments include anchoring elements 120, 125 for secure placement. The cover portion 102a, in other embodiments, can be a separate element that is placed onto the lower body portion 102b and welded, glued, snapped or otherwise secured to form the single shunt 100D. Various welding and bonding techniques can be used to optionally form the planar body portions 102a and 102b into a unitary member with the microchannels 110 therein. This embodiment illustrates partial reservoirs 115A, 115B on both inflow and outflow ports 112A, 112B.

Figure 5:
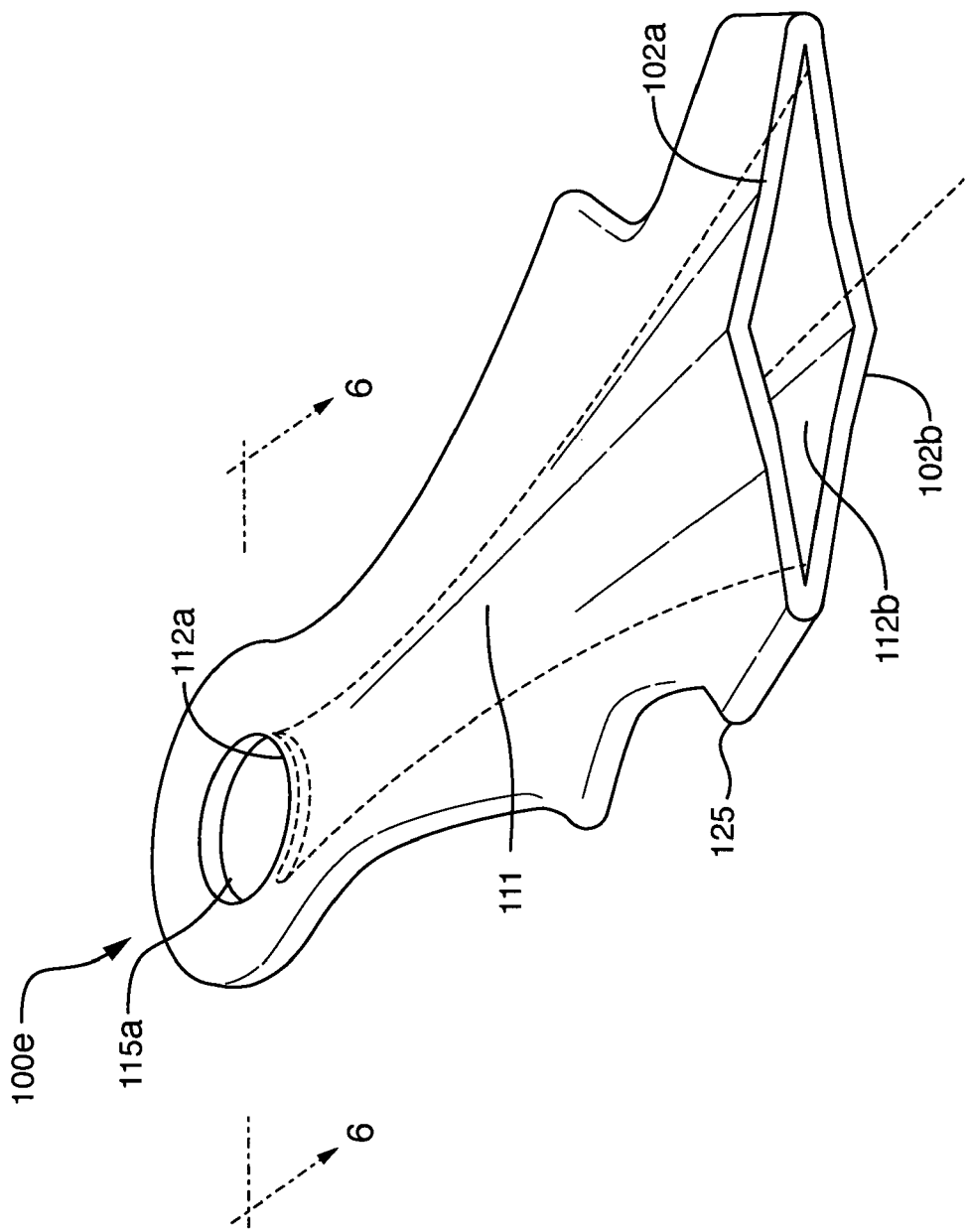
FIG. 5 is a perspective view of an alternative shunt configured in accordance with one embodiment of the present invention and having a single interior flow channel.
Figure 6:
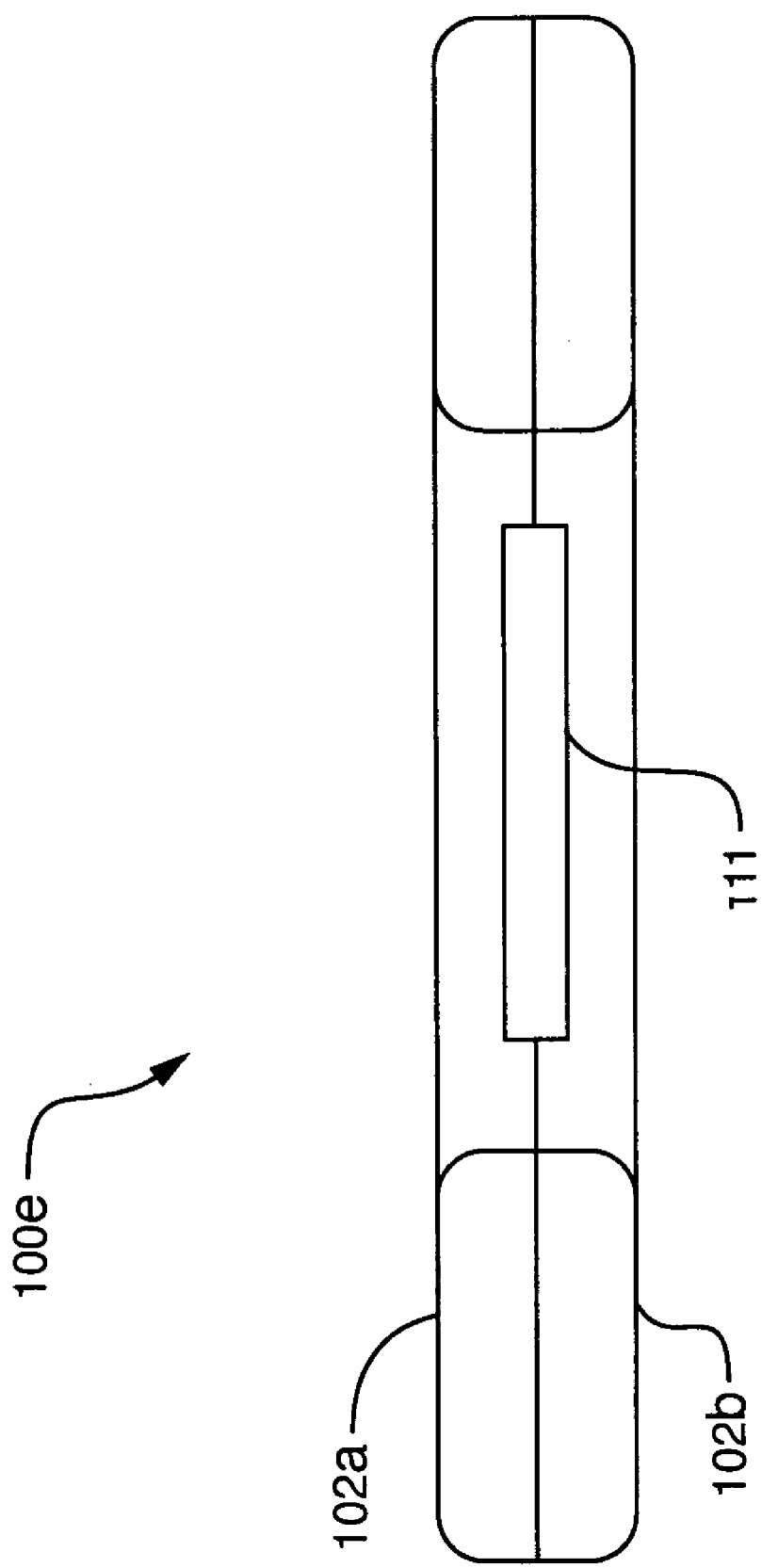
FIG. 6 is an enlarged sectional view of the shunt of FIG. 5 taken along line 6—6 of FIG. 5.

The alternative shunt 100E of FIG. 5 shunt illustrates a device and method of fabrication wherein the planar body portions 102a and 102b are configured to provide a single interior channel 111 through the shunt 100E. The body portions 102a and 102b can be deformed or otherwise shaped to form the interior channel 111. Welding or other bonding techniques are used to bond the perimeter of the planar body portions 102a and 102b if formed from separate elements. FIG. 6 is a sectional view of the shunt 100E showing the internal channel 111 as a single opening in the edge of the inflow port 112A allowing the flow of liquid from the reservoir 115A through the channel 111. The opening on either side of the channel 111 can be similar in overall size/area or have different size/area depending upon the application.

Figure 7:
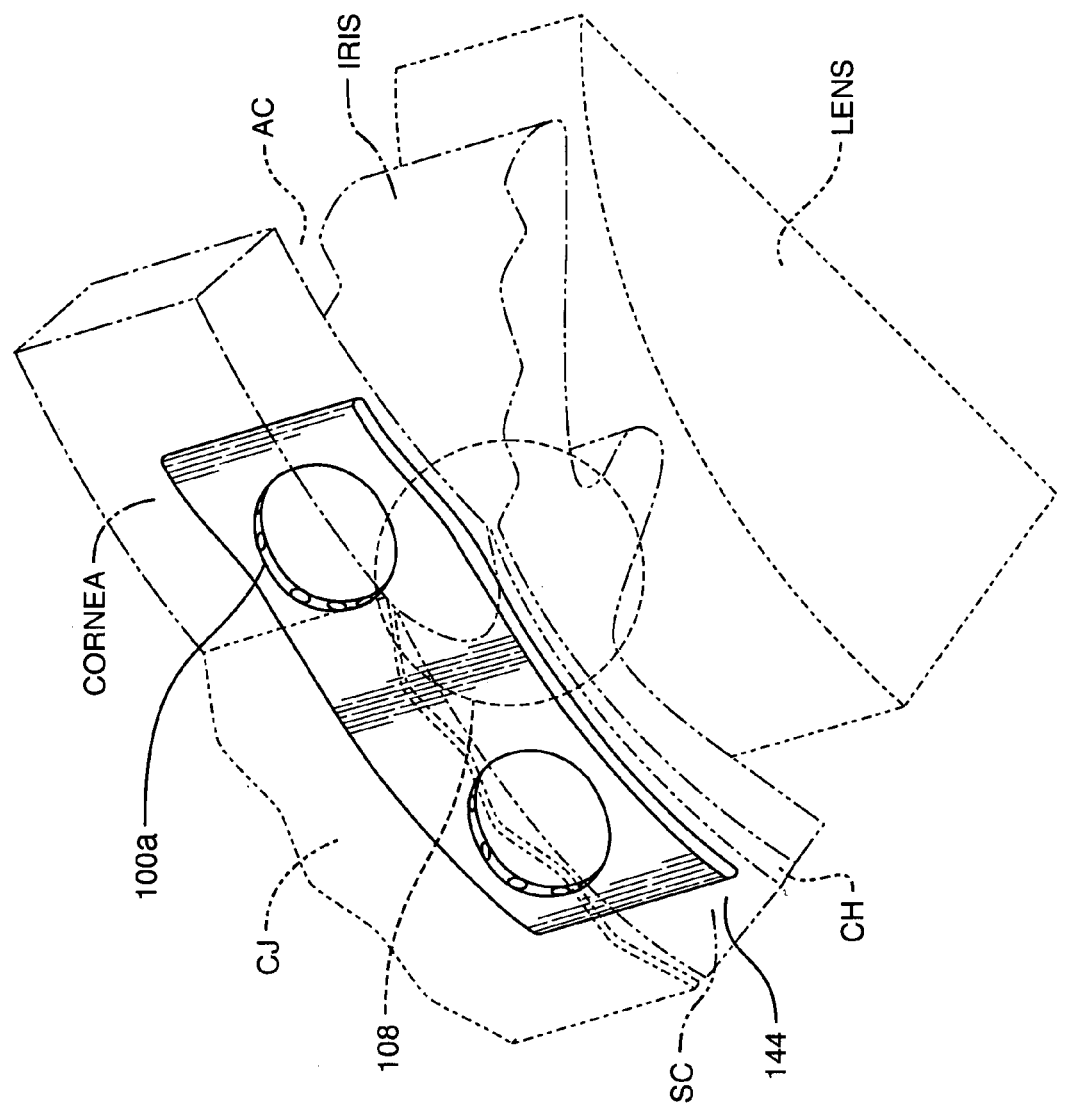
FIG. 7 is a simplified partial view of an eye illustrating an implanted shunt configured in accordance with one embodiment of the present invention.

Now turning to FIG. 7, a simplified view of a patient's eye is shown with the shunt 100A of FIG. 1 implanted in an implant location in a plane that extends from the posterior stromal layers of the cornea through a plane 144 proximate the choroids CH. The schematic view of the eye shows the lens, iris and cornea about the anterior chamber 108. As can be seen in FIG. 7, the final location of the shunt is shown with the sclera SC and conjunctiva CJ being shown as partly transparent, wherein the inflow end is proximate the angle of the anterior chamber. The shunt 100A can be introduced into the eye in various manners as will be described herein in further detail.

Figure 8:
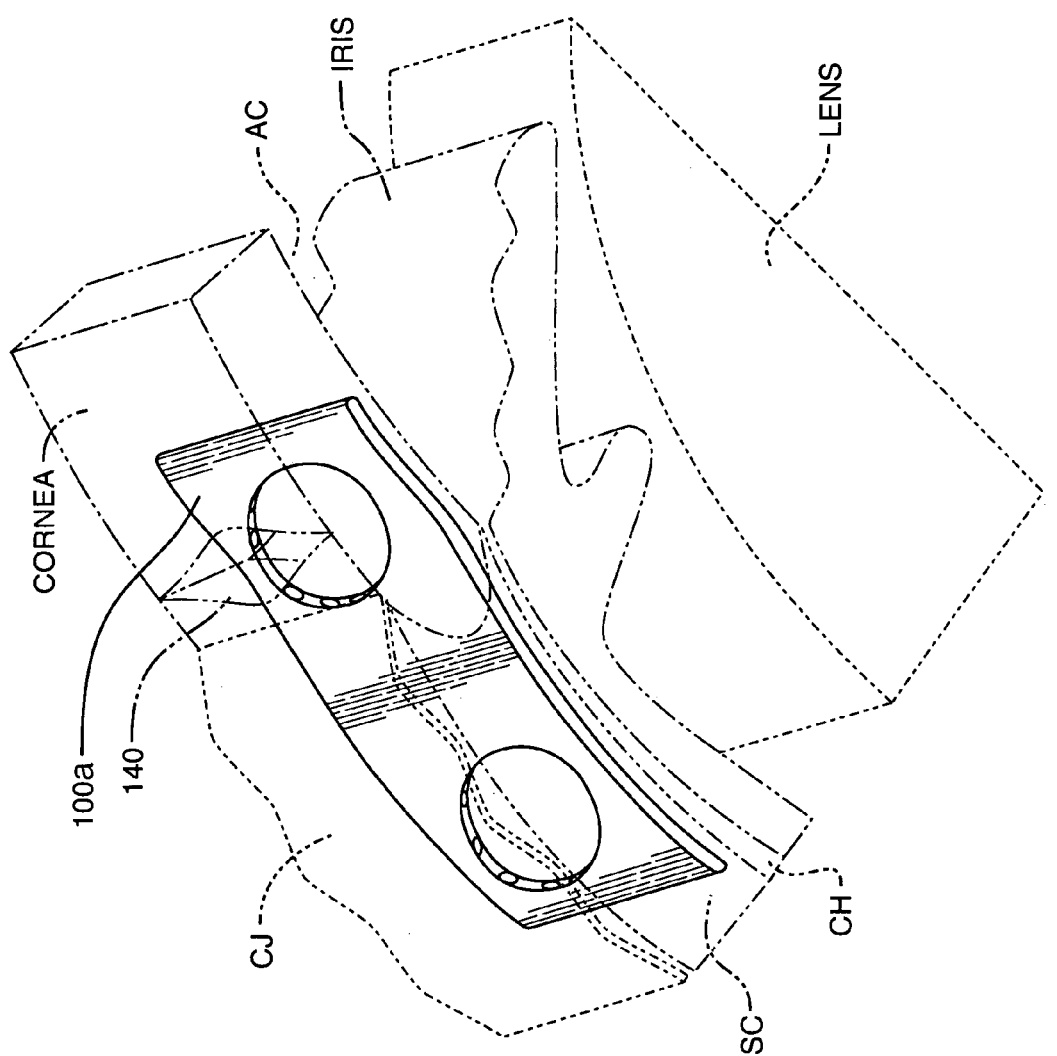
FIG. 8 is a view of an eye as in FIG. 7 illustrating a step in the method of the invention in retracting tissue to allow photo-ablation of tissue proximate to the shunt configured in accordance with one embodiment of the present invention.

FIG. 8 illustrates a step in the method of the invention wherein an incision or penetration 140 is provided over the open portion 115A of shunt 100A. The incision can be the original access incision made for introducing the shunt or a later-made incision to access the plane 144 of the shunt.

Figure 9:
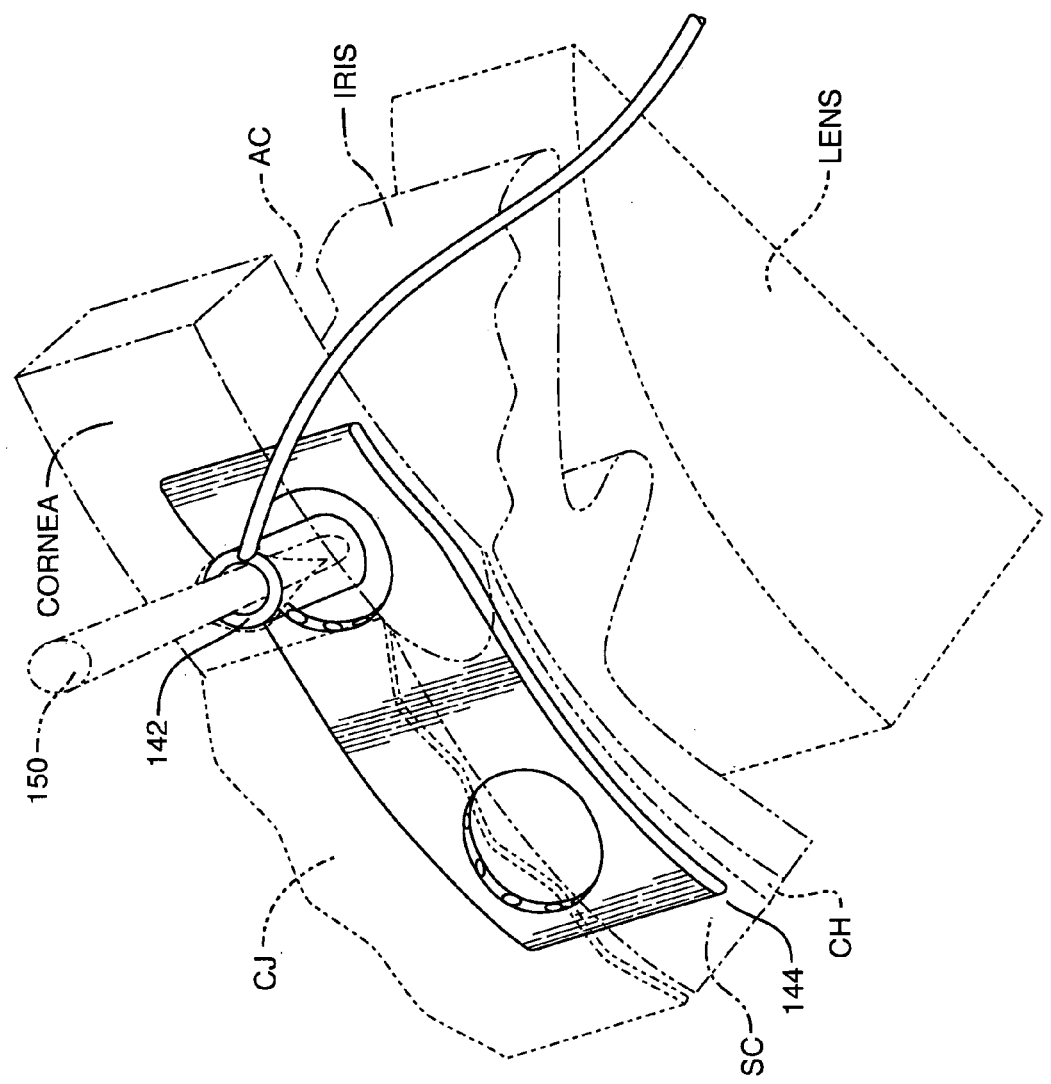
FIG. 9 is a view of an eye as in FIGS. 7–8 illustrating a perspective view of a step in the method of the invention in photo-ablating tissue to create thin tissue layer overlying the reservoir portion of the shunt configured in accordance with one embodiment of the present invention.
Figure 10:
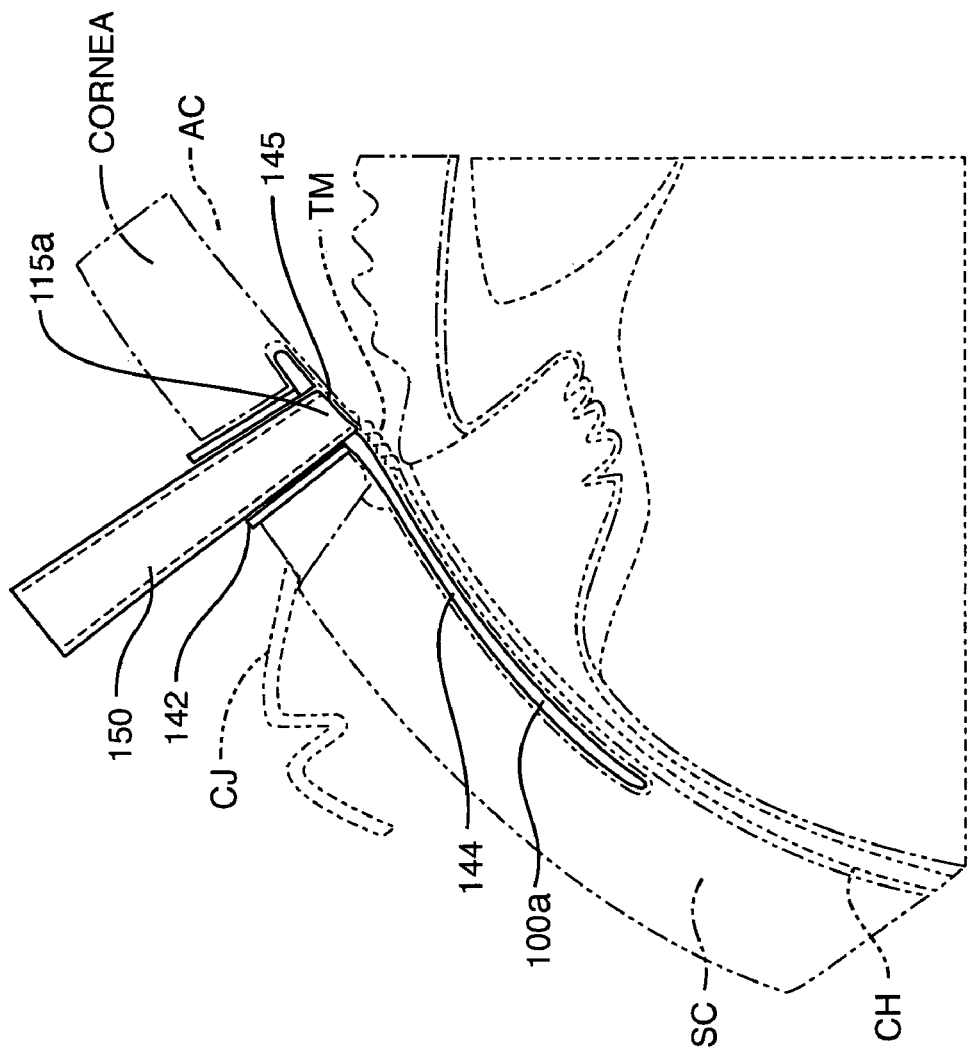
FIG. 10 is a sectional view of the step in FIG. 9 illustrating the photo-ablation of the tissue layer that separates the dissected plane and the anterior chamber.
Figure 11:
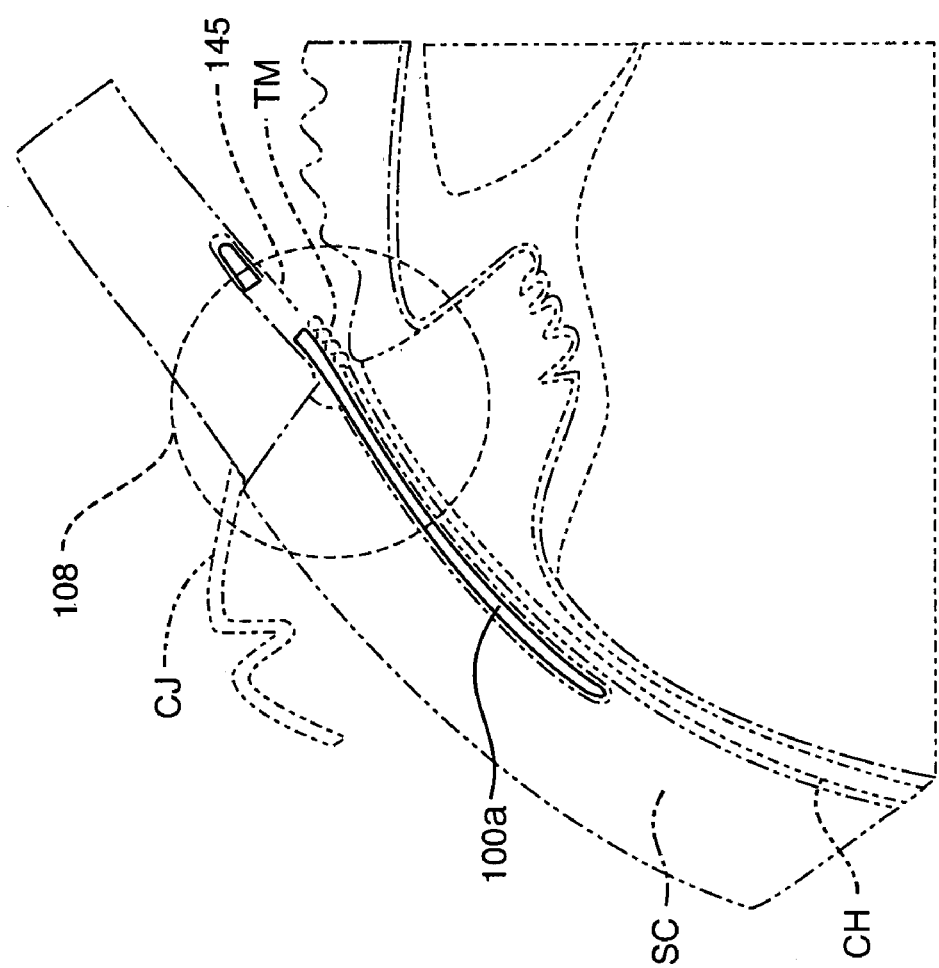
FIG. 11 illustrates the substantially thin tissue layer underlying the open portion of the shunt configured in accordance with one embodiment of the present invention after completion of the implant procedure.

FIGS. 9 and 10 illustrate the next step in a manner of practicing the method of the invention wherein photo-ablation means are utilized to thin the tissue layers 145 that separate the plane 144 of the shunt from the anterior chamber AC. The ablation means can comprise any type of laser, and, in a method according to one embodiment, is an excimer laser together with a scanning system as is known in the art and commonly used for LASIK procedures. Those skilled in the art can readily appreciate how the laser beam indicated at 150 is used to create a desired thickness of tissue 145 underlying the open portion 115A of the shunt 100A. The laser power levels, pulse widths, repetition rates, beam profile, and scan rates all can be compared to the parameters used in LASIK procedures. The sectional view of FIG. 11 illustrates the substantially thin tissue layer 145 underlying open portion 115A of the shunt 100A that will allow controlled flow of aqueous from the anterior chamber AC into open portion 115A of the shunt and thereafter through the microchannels 110 of the shunt. FIGS. 9 and 10 further illustrates the placement of retraction means 142 within the incision 140.

Figure 12:
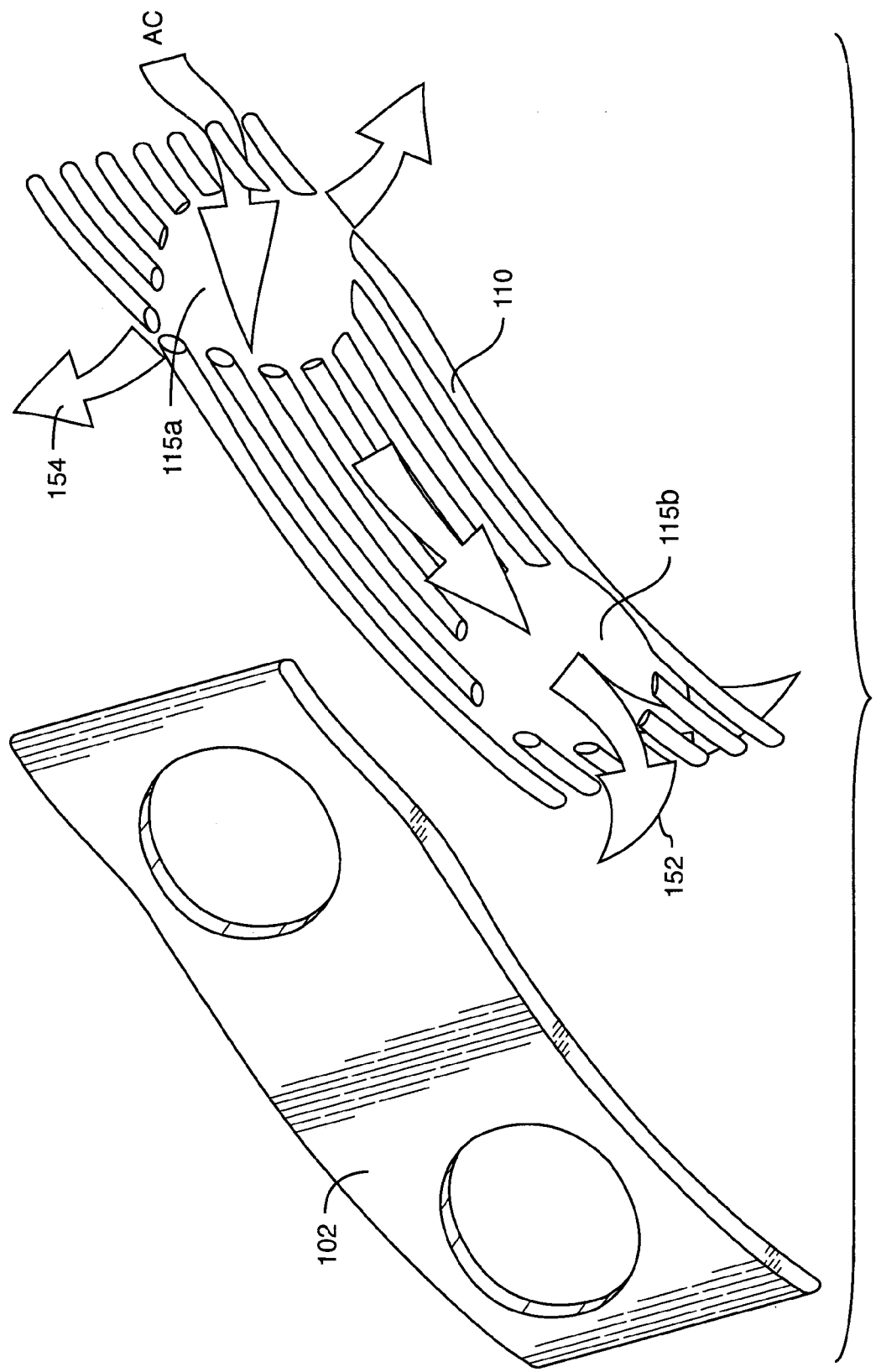
FIG. 12 is schematic illustration of the microchannels and the aqueous flows from the anterior chamber.

FIG. 12 provides a schematic view of the structure of microchannels 110 separated from the shunt body 102 to illustrate the aqueous flows from the anterior chamber AC through the microchannels 110 to exit the second open portion 115B indicated by arrows 152 to be absorbed within the suprachoroidal plane 144. Arrows 154 also indicate that aqueous flows when initially captured within the first second open portion 115A may flow within Schlemm's canal and thereafter through the collectors as in the natural outflow mechanisms.

Figure 13:
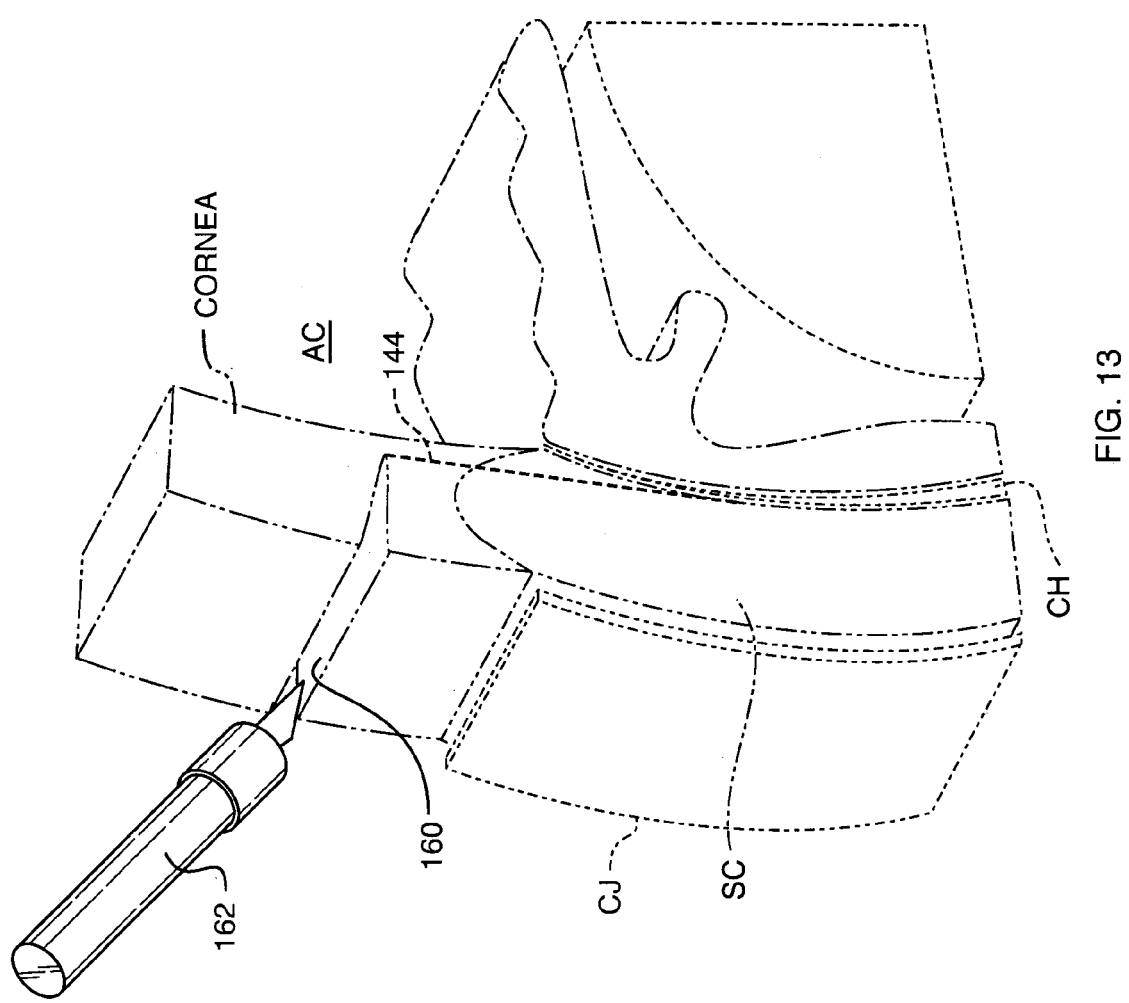
FIG. 13 is a first step in the implanting method of the invention wherein the physician makes a corneal incision under the conjunctiva to a suitable depth in a targeted plane.

Now referring to FIGS. 13 to 20, a method of introducing a shunt configured according to one embodiment of the present invention into its final location is illustrated in a step-wise manner. In FIG. 13, the physician's surgical technique includes making a corneal incision 160 under the conjunctiva CJ to a suitable depth to reach the desired plane 144. The incision can be from 500 to 650 microns or more and can be performed with a round bottom bevel knife 162, for example having a width of about 2.8 mm. The anterior chamber AC is not penetrated. A forceps can be used to open the incision.

Figure 14:
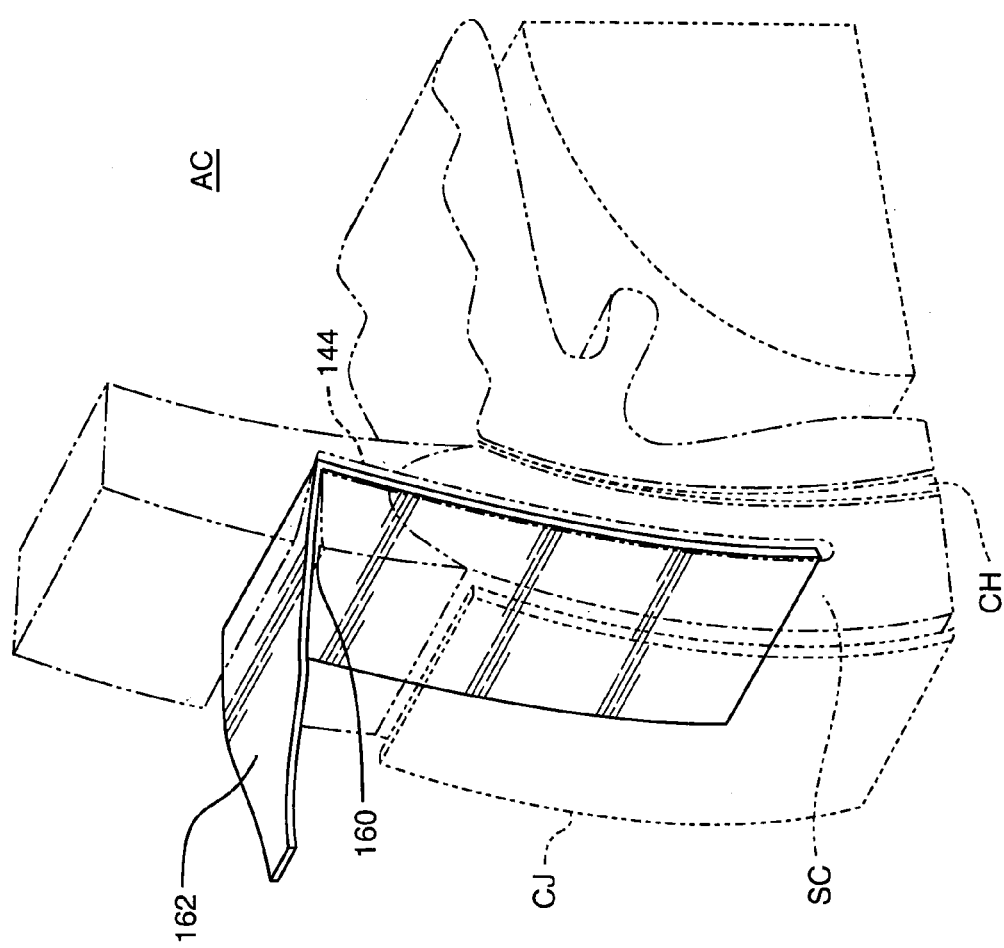
FIG. 14 is another step wherein the physician utilizes a blade to dissect a plane to receive the shunt.

As can be seen in FIGS. 14 and 15, a knife blade 162 is advanced within the desired suprachoroidal plane 144 to create a space to receive the shunt. Alternatively, as can be understood from FIG. 14, a special knife blade can be configured to carry and deploy a shunt so that the blade sharply dissects the desired suprachoroidal plane 144 and then deploys the shunt upon withdrawal of the blade all in a single step. It has been found that implantation of a shunt in this manner can be performed in about one minute in the hands of a practiced surgeon. The incision 160 need not be sutured because of its small size, but sutures can be used if desired.

Figure 16:
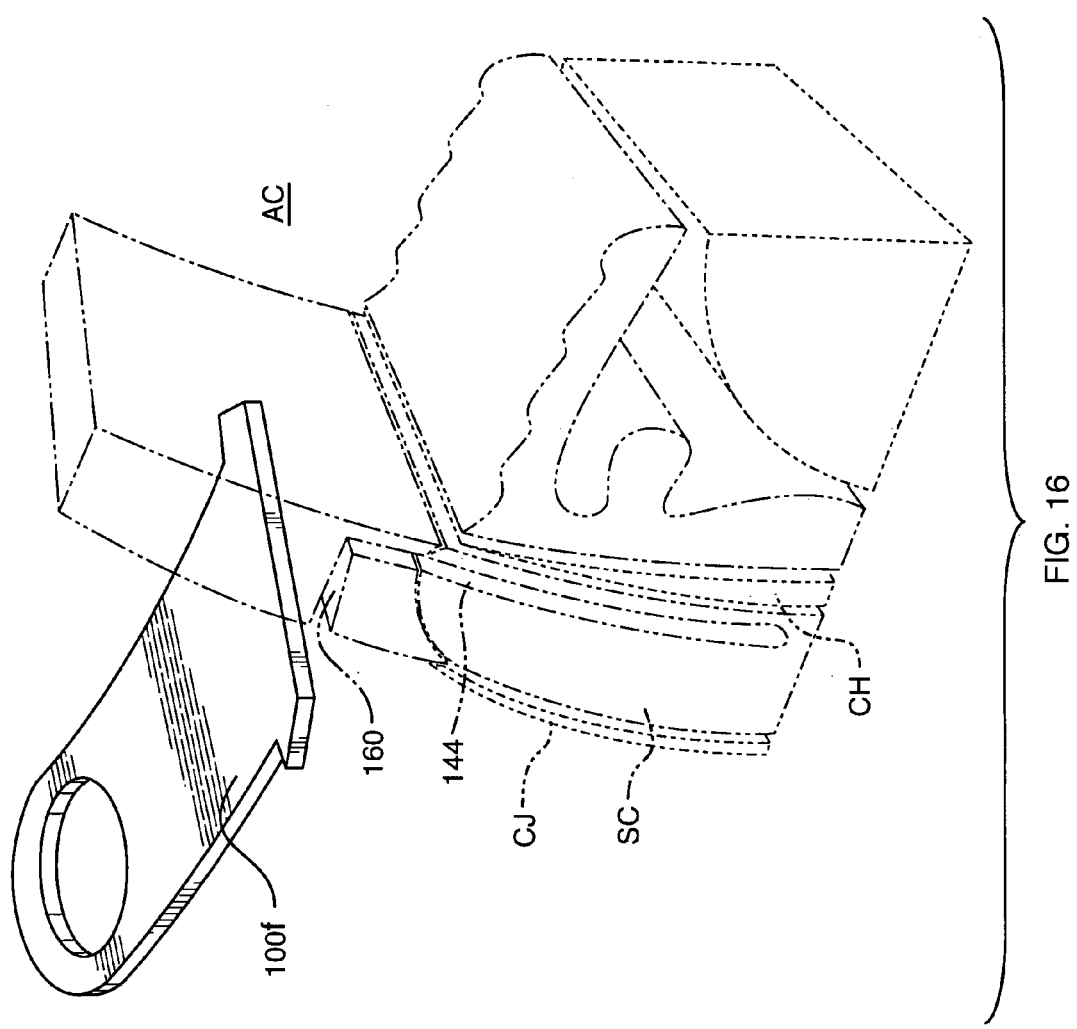
FIG. 16 illustrates an exemplary shunt about to be advanced into the dissected plane.
Figure 17:
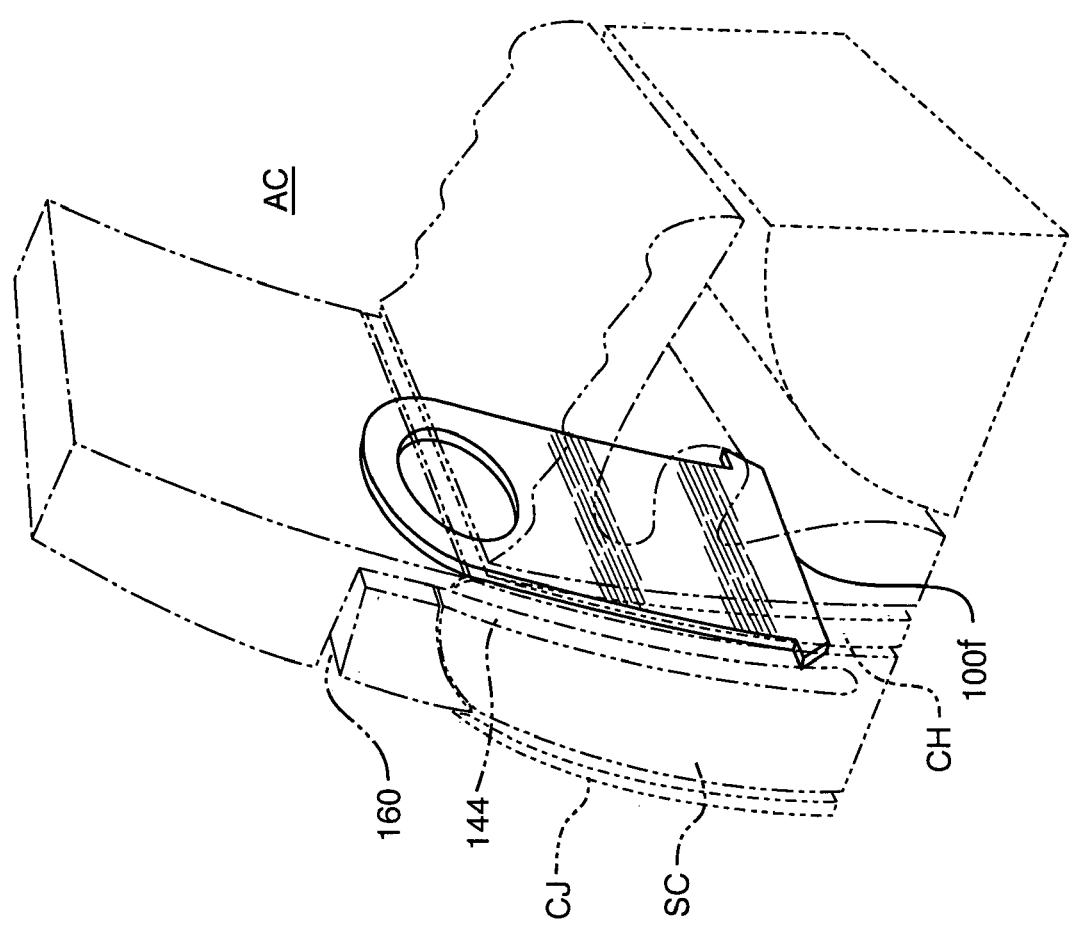
FIG. 17 illustrates the shunt of FIG. 16 implanted in the dissected plane.
Figure 18:
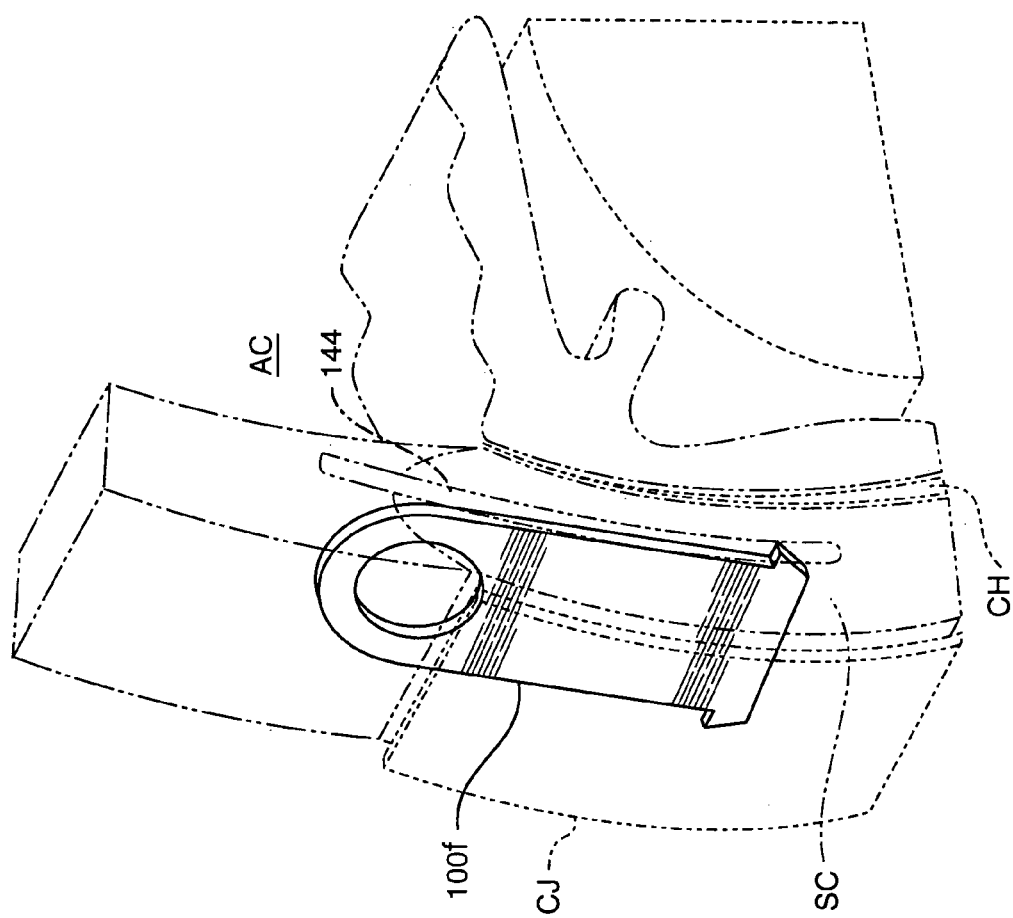
FIG. 18 illustrates another view of the shunt of FIG. 16 implanted in the dissected plane.

FIGS. 16 to 18 illustrate an exemplary shunt 100F being introduced into its final location in plane 144. The subsequent optional photo-ablation of the tissue proximate the shunt can then be performed as described herein if required.

Figure 19C:
FIG. 19 is a schematic view of an alternative shunt that had photo-sacrificial portions for post-implant opening of additional channels.
Figure 19B:
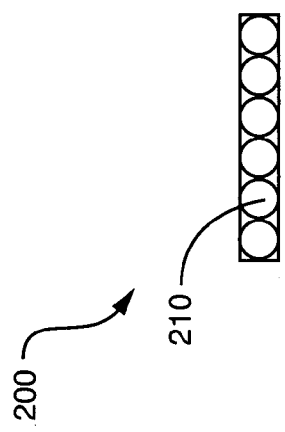
Figure 19A:
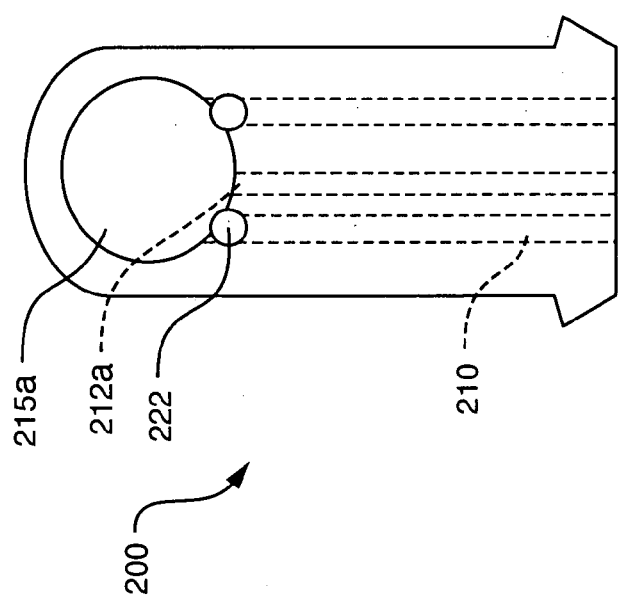

FIG. 19 is a schematic view of an alternative shunt 200 that is introduced into a dissected plane 144 as described above. Of particular interest, this embodiment of the shunt carries additional functionality for allowing post-implant modification or increase of the aqueous outflow rate. The shunt 200 again has a microchannel array 210 with inflow ports 212A about the edge of open region 215A. In this embodiment, that microchannel array 210 comprises at least one channel terminating in inflow port 212A that has a "closed-end" condition when the shunt is implanted. The closed-end of the selected microchannels 222 are illustrated in FIG. 19. In one embodiment, the shunt may carry from 25 to 100 microchannels with about one-half having being in a closed-end condition in its pre-deployed state.

Figure 20:
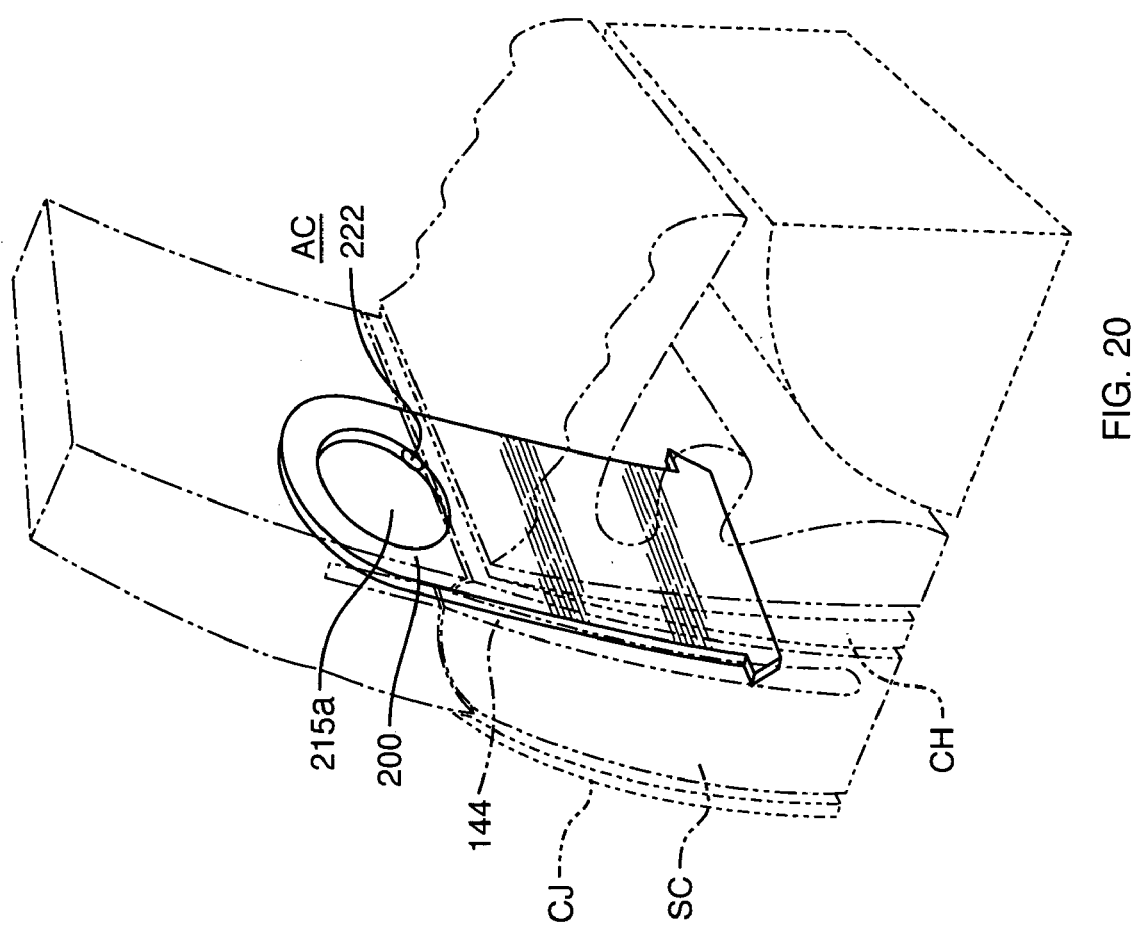
FIG. 20 is a view of a patient's eye with the shunt of FIG. 19 implanted therein with the photo-sacrificial portions viewable through the cornea.
Figure 21:
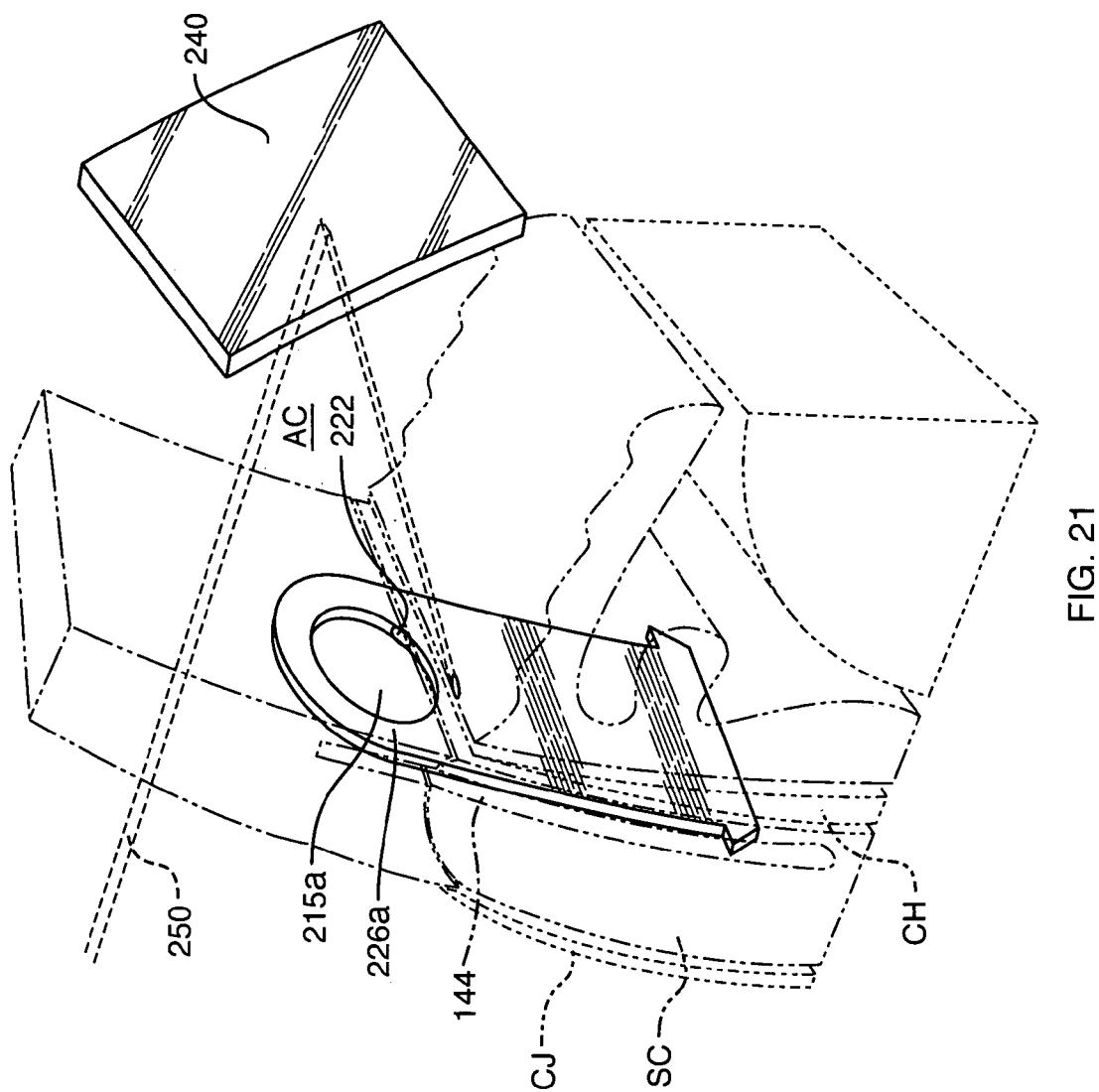
FIG. 21 illustrates a method of the invention wherein a goniolens (schematically indicated) is used to direct a laser beam at the photo-sacrificial portion of the shunt to open a microchannel.

In one embodiment, as can be understood from FIGS. 19 to 21, the closed-end 222 of a plurality of microchannels comprises a sacrificial region that can be photo-ablated to open the "potential" inflow end 212A of the channel. The photo-ablation of the closed-end channel can be accomplished with an excimer laser through an incision, for example as in FIGS. 9 and 10. In one embodiment, the photo-ablation of the closed-end channel or channels is accomplished with a suitable laser in a trans-corneal manner with any suitable wavelength that cooperates with a chromophore in the targeted closed-end media. In one shunt embodiment, the closed-end channel 222 can simply comprise a thin wall portion of the shunt body (with a marker, indentation or the like) that is located over the inflow end 212A of the channel 210. For example, a shunt of gold can have a thin perforatable layer over the end of the microchannel 210 that can be opened with the excimer irradiation. In another embodiment, a photo-ablatable plug 222 can be provided, for example of a chromophore-doped resorbable polymer such as a polyhydroxyalkanoate, polyglycolide, polylactide, poly-caprolactone or any other resorbable polymer.

Figure 22:
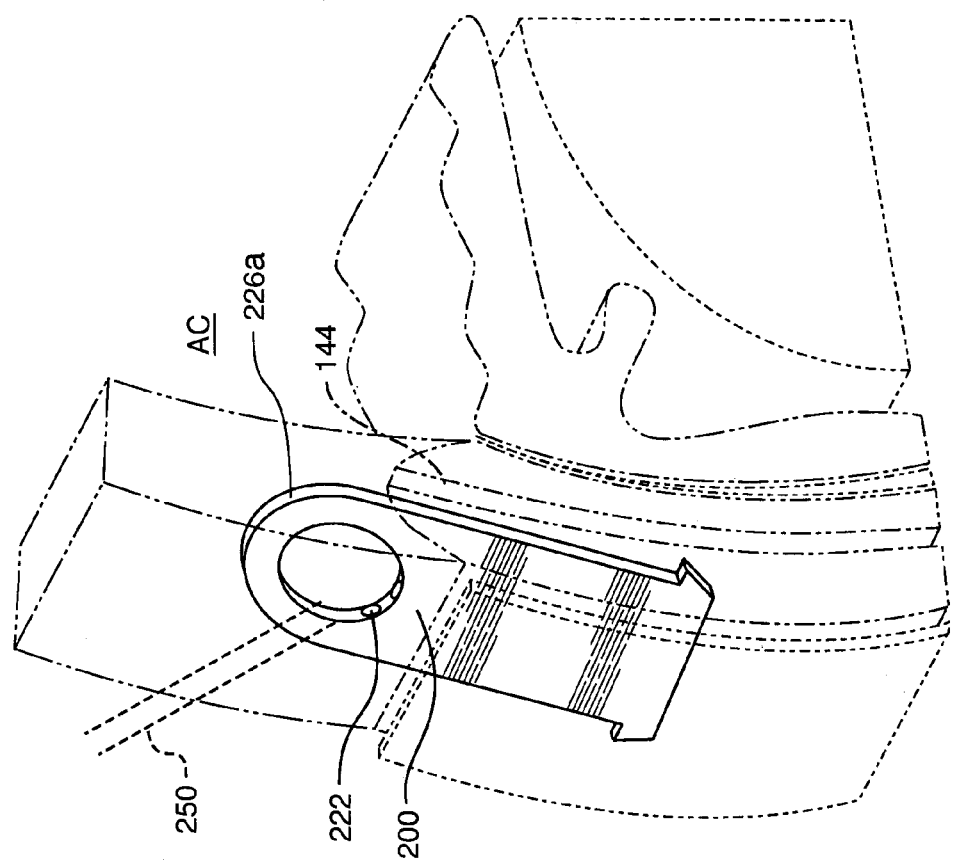
FIG. 22 illustrates another method of the invention wherein a laser beam is aimed directly at a photo-sacrificial portion of the shunt to open a microchannel.

In FIG. 21, a schematic view of the use of a goniolens 240 illustrates laser beam 250 ablating the closed-end 222 of a microchannel 210 to increase outflows. As can be seen in FIGS. 20 and 21, the shunt 200 is implanted so that its first end 226A is well within the cornea to allow ease of targeting the closed-end 222 through the transparent stromal layers. Other variations within the scope of the invention includes (a) direct trans-corneal targeting of the closed-end 222 portions or (b) indirect trans-corneal targeting of closed-end 222 by means of a goniolens 240. FIG. 22 depicts a direct targeting of a closed-end 222 of a microchannel with laser beam 250.

Figure 23:
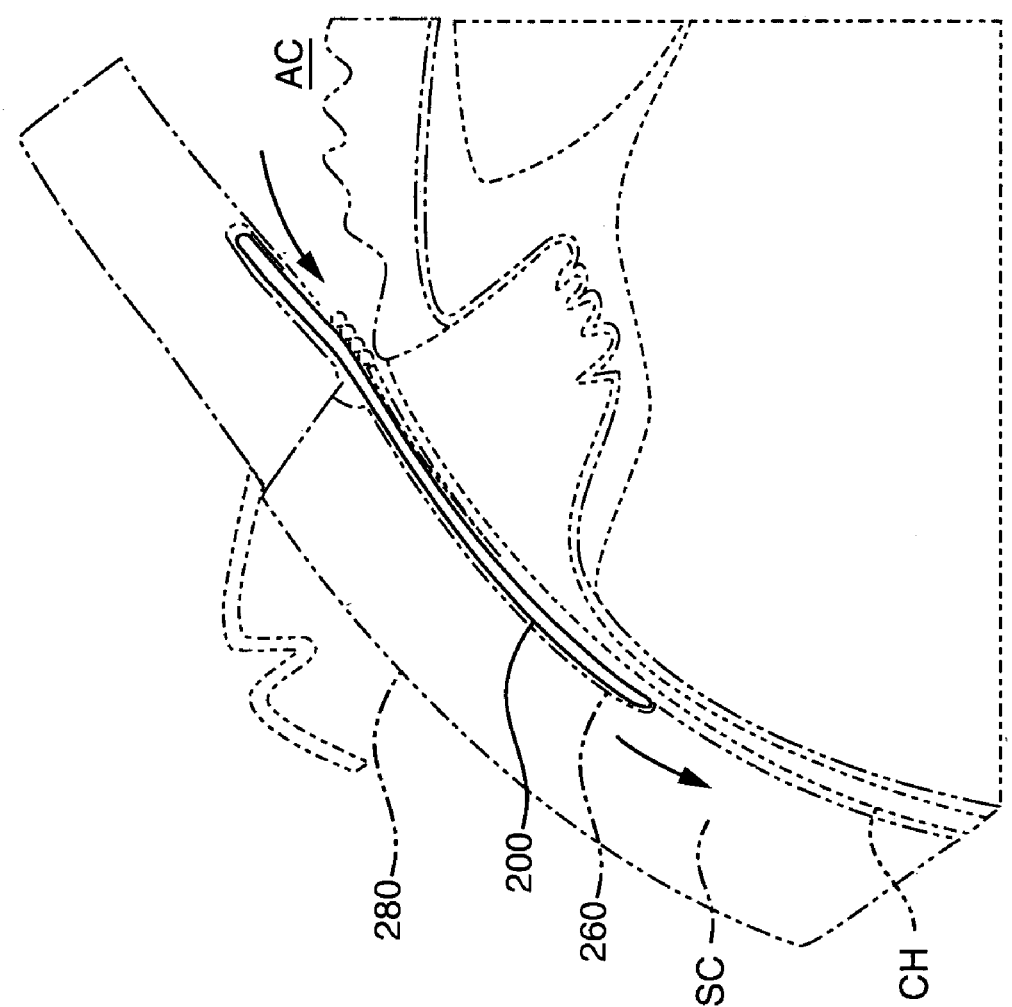
FIG. 23 illustrates a shunt corresponding to the invention wherein the first (inflow) end of the shunt is within the posterior stromal layers proximate the anterior chamber and the second (outflow) end of the shunt is in a suprachoroidal plane.
Figure 24:
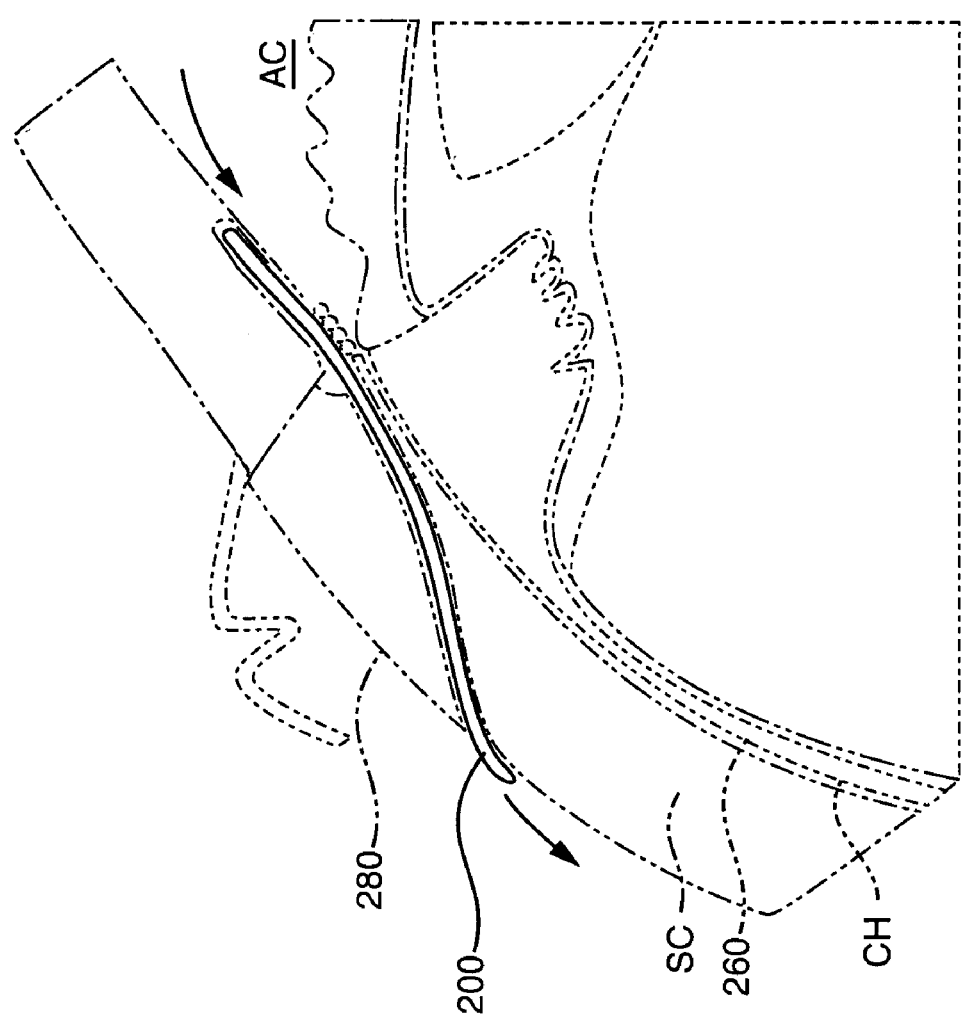
FIG. 24 illustrates an exemplary shunt wherein the first (inflow) end of the shunt is within the posterior stromal layers proximate the anterior chamber and the second (outflow) end of the shunt is in a suprascleral plane.
Figure 25:
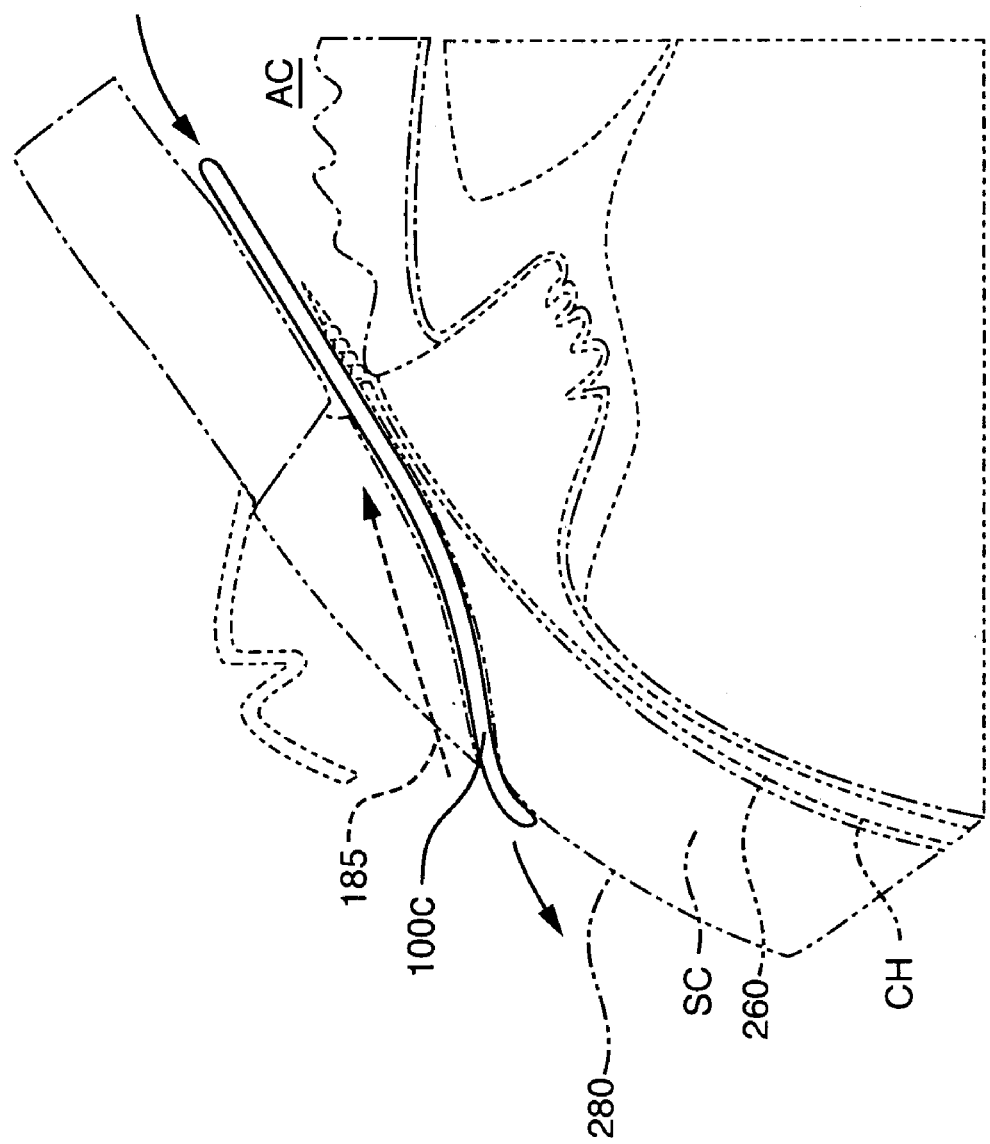
FIG. 25 illustrates an exemplary shunt wherein the first (inflow) end of the shunt is within the anterior chamber and the second (outflow) end of the shunt is in a suprascleral plane.

Now turning to FIGS. 23–25, the scope of the invention includes the methods of implanting any shunt corresponding to the invention in several different orientations, all adapted to carry aqueous humor away from the anterior chamber AC. These orientations can be defined generally by (a) the location of the first end portion 106A of the shunt 100A (see FIG. 1) in relation to the anterior chamber, and (b) the location of the second end portion 106B of shunt 100 within the eye. As can be seen in FIGS. 23 and 24, one implant orientation locates the first end portion 106A of shunt 100A beneath a thin tissue membrane proximate the anterior chamber, but the second end portion 106B for outflows can be within the suprachoroidal plane 260 (FIG. 23) or within a suprascleral plane 280 (FIG. 24).

As can be understood from FIG. 25, another implant orientation locates the first end portion 106A of shunt 100C (see FIG. 3) within the anterior chamber AC and the second end portion 106B for outflows can be within the suprachoroidal plane 260 (FIG. 23) or within a suprascleral plane indicated at 280 (FIG. 24). The implant orientation in FIG. 25 illustrates that the introduction of the implant in the direction of arrow 185 is trans-scleral. The implant 100A of FIG. 25 has a planform as generally shown in FIG. 3 wherein the first end section 106A in the anterior chamber has a straight or curved edge without an open (reservoir) portion. In another orientation (not shown) the shunt's second end portion 106B for outflow is within the suprascleral plane 260 (see FIG. 23).

Figure 26:
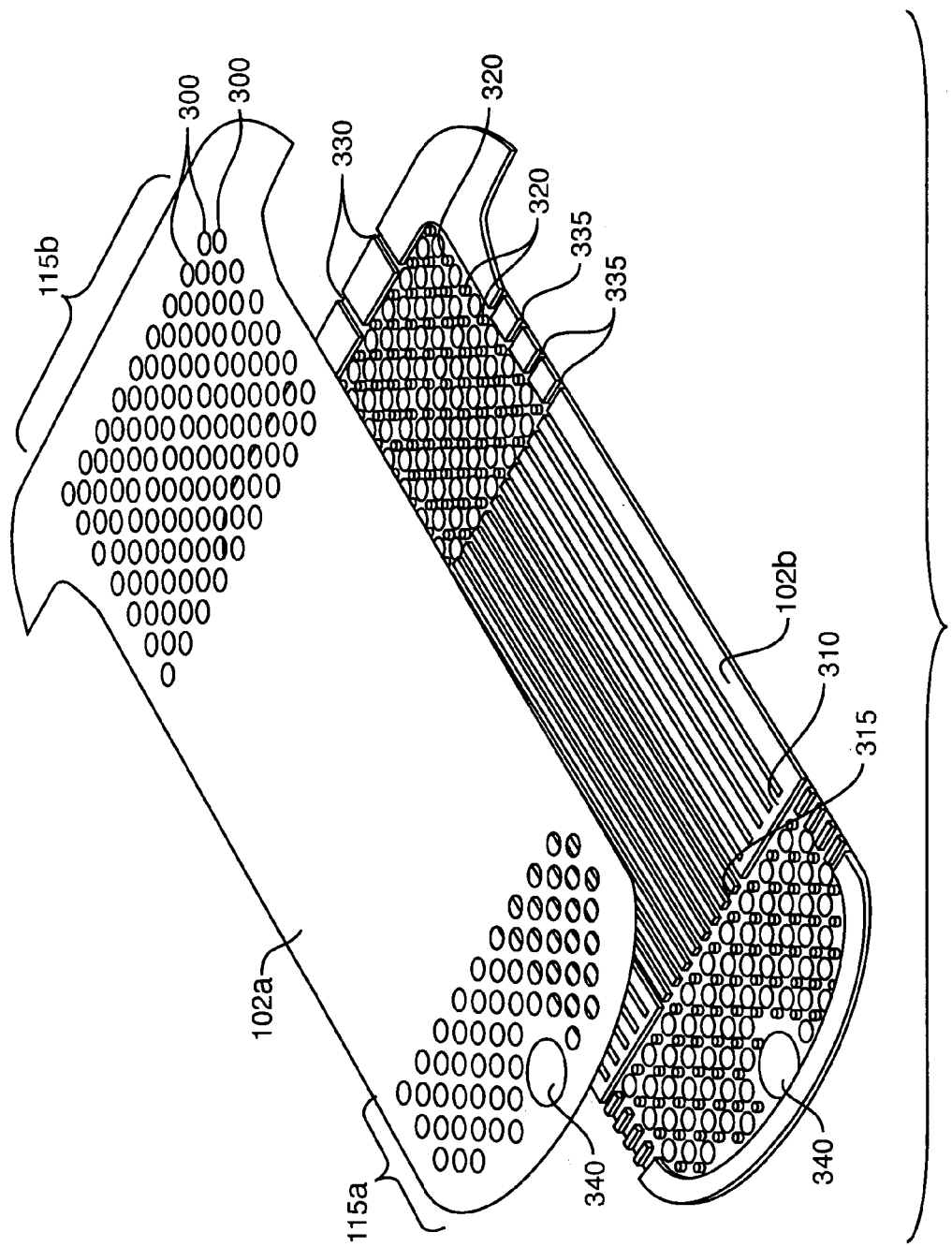
FIG. 26 is a perspective view of a pre-assembly shunt showing the generally planar upper and lower bodies with the microchannels, side channels and front channels disposed therein.

Referring to FIG. 26, a further embodiment of a shunt 100G is illustrated showing various other aspects and variations of the present invention in a 'double sandwich' configuration. The top body portion 102a is shown in close proximity to the lower body portion 102b in this preassembly illustration. The top body portion 102a has a 'screened' reservoir sections 115A, 115B with a plurality of openings or ventilation holes 300. Likewise, the lower body portion 102b has reservoir sections that also employ the screen with a plurality of ventilation holes 300. In the assembled shunt 100G, the ventilation holes 300 allow fluid flow from both sides when placed in the anterior chamber. In one embodiment, the ventilation holes 300 are approximately 100 microns in diameter. There may be larger ventilation holes 300 if desired, and the number and size of the ventilation holes may vary between the inflow reservoir 115A and the outflow reservoir 115B. There may also be a plurality of posts 320 in-between the ventilation holes 300 to provide a space in the reservoir ends and aid in providing structural support to the shunt 100G, wherein the posts 320 in one embodiment are about 30 microns in height and about 50 microns in diameter. In one embodiment, the top body portion 102a mates with the lower body portion 102b such that the holes 300 in the top body 102a are aligned with the holes 300 in the lower body 102b, thereby allowing fluid to enter from either side. A manipulation aid 340 may be provided for implantation, adjustment, and removal of the shunt. The manipulation aid 340 may be a hole, loop, hook, magnet, clip or any other such device known to those skilled in the art that allows the engagement of the shunt by a surgical instrument.

The lower body portion 102b shows open microchannels 315 that connect the reservoirs 115A, 115B, as well as closed microchannels 310. In one embodiment the closed channels 310 are located at the inflow reservoirs 115A and are selectively openable. It is also within the scope of the invention to have open microchannels 315 that are selectively closeable by introducing a blockage or otherwise deliberately restricting channels based upon the IOP. There are various schemes to open and close the microchannels as known in the art or otherwise described herein. In one embodiment the open and closed microchannels 310, 315 are about 50 microns wide with 50 micron spacing.

An additional aspect of the invention is the use of a manipulation hole 340 that aids in holding the shunt 100g during the insertion or extraction process. The oversized hole 340 provides the ability to grasp the shunt 100g with an insertion tool (not shown). While a manipulation hole 340 is shown, there are various other manipulation feature that may be used in conjunction with the insertion tool.

In further embodiment there are one or more front channels 330 that provide additional fluid flow at the endwise edges and in one embodiment the front channels 330 are 50 microns wide and spaced approximately 350 microns apart. There may also at least one side channel 335 that can be formed on any or all of the sides of the shunt 100G to further allow fluid flow. In one embodiment the side channels 335 are 50 microns wide with 50 micron spacing on the inflow end and 50 microns wide with 150 micron spacing on the outflow reservoir. It should be understood that the number and size of the front and side channels is dependent upon the desired application.

As the shunt 100g is intended as a less costly mechanism for glaucoma treatment, the present invention has been designed with ease of manufacturing as an additional feature. The size of the holes and channels take into account the capabilities of the manufacturing processes currently available. Improved manufacturing capabilities may alter certain attributes of the shunt and the present description is not to be limited accordingly.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for reducing intraocular hypertension, the system comprising:
an implantable shunt, said implantable shunt comprising;
a planar member;
at least one microchannel disposed within said planar member;
an inflow port disposed proximate to a first end of said microchannel;
an outflow port disposed proximate to a second end of said microchannel;
said inflow port configured such that when said implantable shunt is implanted, said inflow port is located about approximately within the region of an angle of an anterior chamber and said outflow port is disposed in a suprachoroidal plane; and
at least one reservoir communicating with said second end of said microchannel.

2. The system according to claim 1, wherein said planar member has a thickness less than 50 microns.

3. The system according to claim 2, wherein said thickness of said planar member is between 5 and 25 microns.

4. The system according to claim 1, further comprising at least one anchor.

5. The system according to claim 4, wherein said anchor is selected from the group consisting of barbs, hooks, and sutures.

6. The system according to claim 1, further comprising at least one reservoir communicating with said first end of said microchannel.

7. The system according to claim 1, wherein said at least one microchannel comprises fewer than 200 microchannels.

8. The system according to claim 1 wherein flow of aqueous fluid from said anterior chamber is modulatable.

9. The system according to claim 8 wherein said at least one microchannel comprises a plurality of microchannels, about approximately 40% of microchannels in said plurality of microchannels being configured to be opened.

10. The system according to claim 1, further comprising at least one sacrificial microchannel closure.

11. The system according to claim 10, wherein said closure is photo-ablatable.

12. The system according to claim 10, wherein said closure is doped with chromophores.

13. The system according to claim 1, wherein said at least one microchannel comprises between 10 and 100 microchannels.

14. The system according to claim 1, wherein said system is comprised of at least one biocompatible material selected from the group of materials consisting of gold, platinum, stainless steel, titanium, nickel, molybdenum, biocompatible metals, biocompatible metal alloys, biocompatible ceramics, biocompatible polymers and combinations thereof.

15. A method for the reduction of intraocular pressure in an eye of a subject, said method comprising:

providing an implantable generally planar microchannel shunt;

implanting said shunt in said eye, such that a first end of said shunt is disposed proximate to an angle of an anterior chamber of said eye and a second end is disposed in a suprachoroidal plane; and permitting aqueous flows to migrate from said anterior chamber through at least one microchannel disposed within said shunt; and photo-ablating a sacrificial microchannel closure, thereby increasing flow of said aqueous flow through said shunt.

16. The method according to claim 15, further comprising disposing photo-ablating tissue between said first end and said anterior channel.

17. The method according to claim 15, further comprising: retracting tissue anterior to the first end of said shunt; and photo-ablating an intervening tissue layer with a laser.

18. The method according to claim 15, wherein said photo-ablating comprises using a goniolens.

19. The method according to claim 15 further comprising a modulation of aqueous fluid flow.

20. The method according to claim 15 further comprising introducing a hydrophilic polymer during said implanting.

21. An implantable shunt for glaucoma, said shunt comprising:
a generally planar structure having a first end and a second end;
at least one microchannel disposed within said planar structure, said microchannel substantially extending from said first end to said second end, wherein said first end is implanted proximate an angle of an anterior chamber of an eye and said second end is implanted in a suprachoroidal plane; and at least one outflow reservoir coupled to said second end.

22. The shunt according to claim 21, wherein said planar structure is a material selected from the group of materials consisting of: gold, platinum, stainless steel, nickel, molybdenum, titanium, biocompatible metals, biocompatible metal alloys, biocompatible polymers and combinations thereof.

23. The shunt according to claim 21, further comprising at least one front channel in said structure.

24. The shunt according to claim 21, further comprising at least one side channel in said structure.

25. The shunt according to claim 21, wherein said structure is comprised of two generally planar bodies coupled together with said microchannels disposed therebetween.

26. The shunt according to claim 21, wherein said generally planar structure has a shape selected from the group consisting of concave, convex, and substantially planar.

27. The shunt according to claim 21, wherein said structure has a variable thickness.

28. The shunt according to claim 21, wherein at least one of said microchannels are closed microchannels.

29. The shunt according to claim 28, wherein said closed microchannels are selectively openable.

30. The shunt according to claim 21, further comprising at least one inflow reservoir coupled to said first end.

31. The shunt according to claim 21, wherein said inflow reservoir and said outflow reservoir have ventilation holes.

32. The shunt according to claim 21, further comprising a coating.

33. The shunt according to claim 32, wherein said coating is a coating selected from the group of coatings consisting of mineral coatings, pharmaceutical coatings, radiological coatings, polymer coatings, metallic coatings, and combinations thereof.

34. The shunt according to claim 21 further comprising a manipulation aid.

* * * * *